United States Patent
Pattison et al.

(10) Patent No.: US 10,219,799 B2
(45) Date of Patent: Mar. 5, 2019

(54) TRANSABDOMINAL GASTRIC DEVICE AND METHOD

(71) Applicant: ENDO-TAGSS, LLC, Leawood, KS (US)

(72) Inventors: Mary Pattison, Kansas City, MO (US); Charles Phillip Pattison, Kansas City, MO (US); Stephen J. Lowry, Kansas City, MO (US); Mark Molos, Kansas City, MO (US)

(73) Assignee: ENDO-TAGSS, LLC, Leawood, KS (US)

( * ) Notice: Subject to any disclaimer, the term of this patent is extended or adjusted under 35 U.S.C. 154(b) by 941 days.

(21) Appl. No.: 14/554,337

(22) Filed: Nov. 26, 2014

(65) Prior Publication Data

US 2015/0150595 A1 Jun. 4, 2015

Related U.S. Application Data

(63) Continuation-in-part of application No. PCT/US2014/049639, filed on Aug. 4, 2014, and a
(Continued)

(51) Int. Cl.
*A61B 17/34* (2006.01)
*A61B 17/02* (2006.01)
*A61B 17/00* (2006.01)

(52) U.S. Cl.
CPC ...... *A61B 17/0218* (2013.01); *A61B 17/3415* (2013.01); *A61B 17/3462* (2013.01);
(Continued)

(58) Field of Classification Search
CPC ........ A61B 17/3423; A61B 2017/3466; A61B 2017/3441; A61B 2017/3427;
(Continued)

(56) References Cited

U.S. PATENT DOCUMENTS

| 4,315,513 A | 2/1982 | Nawash et al. |
| 4,356,824 A | 11/1982 | Vasquez |

(Continued)

FOREIGN PATENT DOCUMENTS

| WO | WO2007/136683 | 11/2007 |
| WO | WO2010/087690 | 8/2010 |

(Continued)

OTHER PUBLICATIONS

U.S. Appl. No. 14/554,677, filed Nov. 26, 2014.
(Continued)

*Primary Examiner* — David Bates
(74) *Attorney, Agent, or Firm* — Leydig, Voit & Mayer, Ltd.

(57) ABSTRACT

Provided herein are trans-abdominal gastric systems and related methods that are useful in a range of applications for accessing internal regions of a patient. A cannula has internal and external anchors to reliably secure the anchor to an abdominal wall of the patient. An introducer with a capture element facilitates system placement by retrograde introduction. Upon completion, the system is removed and the gastric and abdominal wall incision and defect closed by sutures specially connected to the system that ensures reliable system removal and suture closure in a configuration that is outside the abdominal wall. The systems and methods are particularly suited for use with conventional laparoscopic or endoscopic medical instruments.

28 Claims, 29 Drawing Sheets

Related U.S. Application Data continuation-in-part of application No. 14/451,108, filed on Aug. 4, 2014.

(60) Provisional application No. 61/862,357, filed on Aug. 5, 2013, provisional application No. 61/862,358, filed on Aug. 5, 2013.

(52) U.S. Cl.
CPC .............. *A61B 2017/00278* (2013.01); *A61B 2017/349* (2013.01); *A61B 2017/3425* (2013.01); *A61B 2017/3466* (2013.01); *A61B 2017/3482* (2013.01); *A61B 2017/3484* (2013.01); *A61B 2017/3488* (2013.01); *A61B 2017/3492* (2013.01)

(58) Field of Classification Search
CPC .... A61B 2017/3482; A61B 2017/3492; A61B 2017/349; A61B 2017/00637; A61B 2017/00659
See application file for complete search history.

(56) References Cited

U.S. PATENT DOCUMENTS

| | | |
|---|---|---|
| 4,668,225 A | 5/1987 | Russo et al. |
| 5,007,900 A | 4/1991 | Picha et al. |
| 5,071,405 A | 12/1991 | Piontek et al. |
| 5,112,310 A | 5/1992 | Grobe |
| 5,147,316 A | 9/1992 | Castillenti |
| 5,167,627 A | 12/1992 | Clegg et al. |
| 5,259,399 A | 11/1993 | Brown |
| 5,391,159 A | 2/1995 | Hirsch et al. |
| 5,403,290 A * | 4/1995 | Noble ................. F16K 11/0853 137/625.47 |
| 5,527,280 A | 6/1996 | Goelz |
| 5,716,347 A | 2/1998 | Gibbs et al. |
| 5,720,734 A | 2/1998 | Copenhaver et al. |
| 5,865,816 A | 2/1999 | Quinn |
| 5,993,473 A | 11/1999 | Chan et al. |
| 6,030,361 A | 2/2000 | Miyashiro |
| 6,419,670 B1 | 7/2002 | Dikeman |
| 6,454,785 B2 | 9/2002 | De Hoyos Garza |
| 6,551,270 B1 | 4/2003 | Bimbo et al. |
| 6,907,992 B2 | 6/2005 | McMichael et al. |
| 6,910,581 B2 | 6/2005 | McMichael et al. |
| 7,025,791 B2 | 4/2006 | Levine et al. |
| 7,122,058 B2 | 10/2006 | Levine et al. |
| 7,220,284 B2 | 5/2007 | Kagan et al. |
| 7,267,694 B2 | 9/2007 | Levine et al. |
| 7,314,489 B2 | 1/2008 | McKenna et al. |
| 7,316,716 B2 | 1/2008 | Egan |
| 7,329,285 B2 | 2/2008 | Levine et al. |
| 7,347,875 B2 | 3/2008 | Levine et al. |
| 7,476,256 B2 | 1/2009 | Meade et al. |
| 7,563,254 B2 | 7/2009 | Delegge |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,794,447 B2 | 9/2010 | Dann et al. |
| 7,806,870 B2 | 10/2010 | Mastri et al. |
| 7,815,591 B2 | 10/2010 | Levine et al. |
| 7,819,836 B2 | 10/2010 | Levine et al. |
| 7,824,368 B2 | 11/2010 | Clem et al. |
| 7,833,156 B2 | 11/2010 | Williams et al. |
| 7,833,202 B2 | 11/2010 | Suzuki |
| 7,837,643 B2 | 11/2010 | Levine et al. |
| 7,935,073 B2 | 5/2011 | Levine et al. |
| 7,976,488 B2 | 7/2011 | Levine et al. |
| 7,981,163 B2 | 7/2011 | Meade et al. |
| 8,057,420 B2 | 11/2011 | Meade et al. |
| 8,096,966 B2 | 1/2012 | Levine et al. |
| 8,097,000 B2 | 1/2012 | Albrecht |
| 8,109,910 B2 | 2/2012 | Zastawny et al. |
| 8,109,943 B2 | 2/2012 | Boraiah et al. |
| 8,137,301 B2 | 3/2012 | Levine et al. |
| 8,147,454 B2 | 4/2012 | Watanabe et al. |
| 8,147,561 B2 | 4/2012 | Binmoeller |
| 8,162,871 B2 | 4/2012 | Levine et al. |
| 8,182,459 B2 | 5/2012 | Dann et al. |
| 8,206,456 B2 | 6/2012 | Stack et al. |
| 8,211,186 B2 | 7/2012 | Belhe et al. |
| 8,246,617 B2 | 8/2012 | Welt et al. |
| 8,303,669 B2 | 11/2012 | Meade et al. |
| 8,430,811 B2 | 4/2013 | Hess et al. |
| 8,585,733 B2 * | 11/2013 | Newell .............. A61B 17/0469 606/192 |
| 2002/0042607 A1 | 4/2002 | Palmer et al. |
| 2002/0055757 A1 | 5/2002 | Torre et al. |
| 2003/0097099 A1 | 5/2003 | Quinn |
| 2003/0158569 A1 | 8/2003 | Wazne |
| 2003/0225393 A1 | 12/2003 | McMichael et al. |
| 2004/0059289 A1 | 3/2004 | Garza |
| 2005/0049624 A1 | 3/2005 | Francese et al. |
| 2005/0240279 A1 | 10/2005 | Kagan et al. |
| 2005/0267415 A1 | 12/2005 | Jacques |
| 2006/0030872 A1 | 2/2006 | Culbert et al. |
| 2006/0052752 A1 * | 3/2006 | McMichael ......... A61J 15/0057 604/175 |
| 2007/0123840 A1 | 5/2007 | Cox |
| 2007/0156165 A1 | 7/2007 | Chang et al. |
| 2007/0225728 A1 | 9/2007 | Stefanchik et al. |
| 2007/0255257 A1 | 11/2007 | Willis et al. |
| 2008/0249474 A1 | 10/2008 | Baker |
| 2009/0204067 A1 * | 8/2009 | Abu-Halawa ...... A61B 17/3415 604/96.01 |
| 2009/0299486 A1 | 12/2009 | Shohat et al. |
| 2010/0081875 A1 | 4/2010 | Fowler et al. |
| 2010/0081883 A1 | 4/2010 | Murray et al. |
| 2010/0152764 A1 | 6/2010 | Merkle |
| 2010/0249822 A1 | 9/2010 | Nihalani |
| 2010/0280368 A1 | 11/2010 | Can et al. |
| 2010/0312047 A1 | 12/2010 | Forsell |
| 2010/0324375 A1 | 12/2010 | Piskun |
| 2010/0331756 A1 | 12/2010 | Meade et al. |
| 2011/0028793 A1 | 2/2011 | Martin et al. |
| 2011/0046537 A1 | 2/2011 | Errico et al. |
| 2011/0082442 A1 | 4/2011 | Solovay et al. |
| 2011/0106273 A1 | 5/2011 | Belhe et al. |
| 2011/0160539 A1 | 6/2011 | Robertson |
| 2011/0245751 A1 | 10/2011 | Hoffmann |
| 2011/0257580 A1 | 10/2011 | Meade et al. |
| 2011/0276091 A1 | 11/2011 | Melanson et al. |
| 2011/0301523 A1 | 12/2011 | Levine et al. |
| 2012/0029413 A1 | 2/2012 | Meade et al. |
| 2012/0078174 A1 | 3/2012 | Tai et al. |
| 2012/0095495 A1 | 4/2012 | Babkes et al. |
| 2012/0116362 A1 | 5/2012 | Kieturakis |
| 2012/0132212 A1 | 5/2012 | Nishtala |
| 2012/0184967 A1 | 7/2012 | Levine et al. |
| 2012/0203271 A1 | 8/2012 | Larkin et al. |
| 2012/0215152 A1 | 8/2012 | Levine et al. |
| 2012/0232339 A1 | 11/2012 | Csiky |
| 2012/0323081 A1 | 12/2012 | Son |
| 2013/0012862 A1 | 1/2013 | Meade et al. |
| 2013/0041231 A1 | 2/2013 | Bonadio et al. |
| 2013/0041372 A1 | 2/2013 | Welt et al. |
| 2013/0060091 A1 | 3/2013 | Azarbarzin et al. |
| 2013/0066304 A1 | 3/2013 | Belson et al. |
| 2013/0102876 A1 | 4/2013 | Limon et al. |
| 2013/0211196 A1 | 8/2013 | Belson et al. |
| 2014/0058362 A1 | 2/2014 | Tycast et al. |

(56) References Cited

U.S. PATENT DOCUMENTS

2014/0276338 A1    9/2014    Pattison et al.
2015/0038794 A1    2/2015    Pattison et al.

FOREIGN PATENT DOCUMENTS

| WO | WO2011/004335 | 1/2011 |
| WO | WO2011/072096 | 6/2011 |
| WO | WO2015/020977 | 8/2014 |
| WO | WO2014/145799 | 9/2014 |

OTHER PUBLICATIONS

International Search Report and Written Opinion Corresponding to International Application No. PCT/US2014/030625, Completed Aug. 1, 2014.

International Search Report and Written Opinion of the International Searching Authority Corresponding to International Application No. PCT/US2014/049639, Completed Nov. 12, 2014.

International Search Report and Written Opinion of the International Searching Authority Corresponding to International Application No. PCT/US14/67689, Completed Mar. 30, 2015.

International Search Report and Written Opinion of the International Searching Authority Corresponding to International Application No. PCT/US14/67697, Completed Mar. 30, 2015.

Office Action corresponding to U.S. Appl. No. 14/451,108, dated Apr. 6, 2017.

Extended European Search Report corresponding to European Patent Application No. 14835461.6, dated Jun. 16, 2017.

Supplementary Partial European Search Report corresponding to European Patent Application No. 14835461.6, dated Mar. 15, 2017.

Examination Report corresponding to Australian Patent Application No. 2014306164, dated May 15, 2018.

First Office Action corresponding to Chinese Patent Application No. 2014800549229, including English translation, dated Apr. 28, 2018.

Extended European Search Report corresponding to European Patent Application No. 14907024.5, dated Jun. 14, 2018.

\* cited by examiner

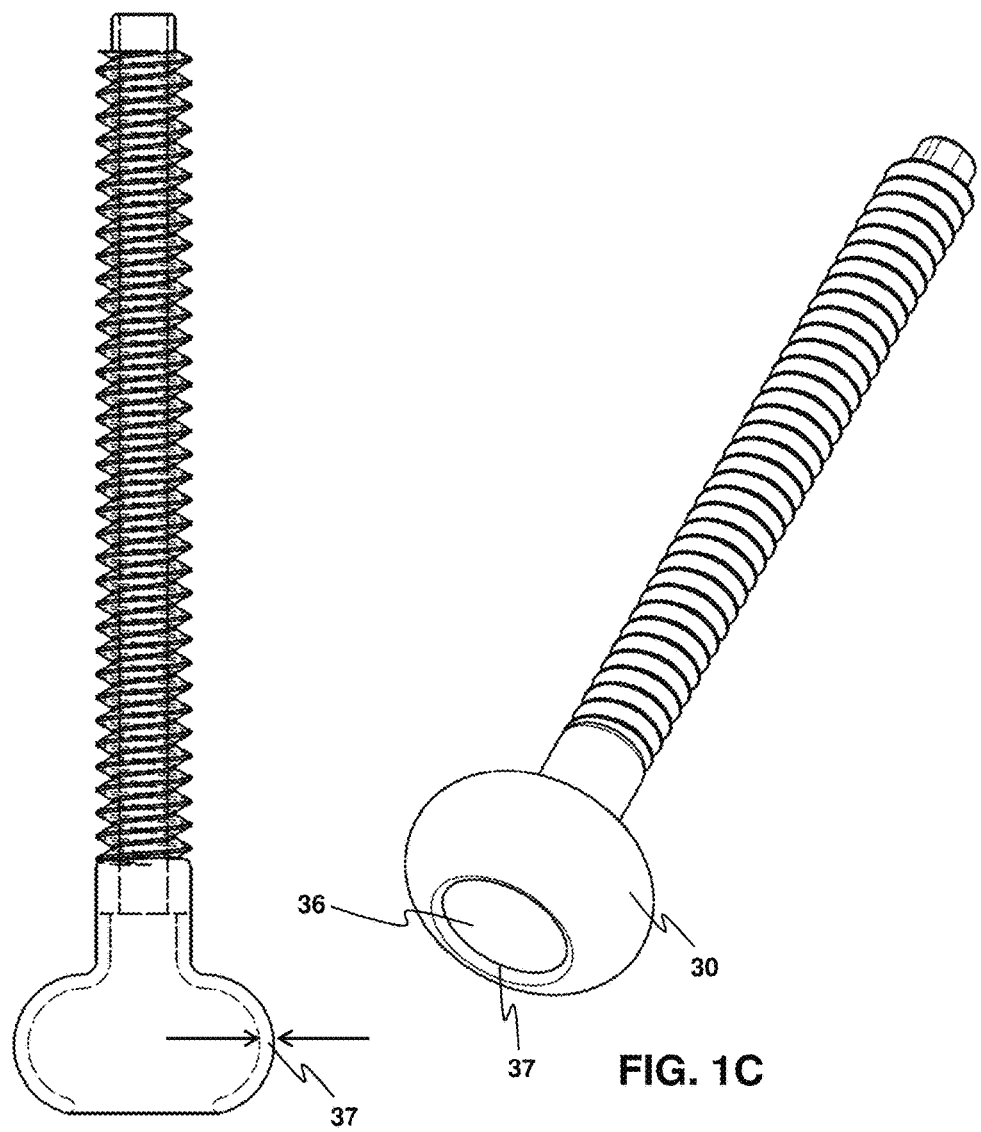

TRANSABDOMINAL GASTRIC DEVICE AND METHOD

CROSS-REFERENCE TO RELATED APPLICATIONS

This application is a continuation-in-part of U.S. patent application Ser. No. 14/451,108 and PCT App. No. PCT/US14/49639, each filed Aug. 4, 2014, each of which claims benefit of U.S. Provisional Application Nos. 61/862,357 and 61/862,358, each filed Aug. 5, 2013, each of which is specifically incorporated by reference to the extent not inconsistent herewith.

BACKGROUND OF INVENTION

Provided herein are systems and methods related to transabdominal access to various internal regions, including the gastric environment, from outside the body. The systems are particularly useful for securably positioning a cannula through the abdominal wall to facilitate access to the gastric environment from outside the patient body. The systems and methods are versatile, providing a platform for intraluminal gastric access, extraluminal gastric access, and/or access of the peritoneal space and related organs using a single or multiple systems. Multiple systems may be used to provide simultaneous access via different cannula locations relative to the stomach lumen and peritoneal space, such as to provide simultaneous access to the intraluminal and extraluminal environment. The systems and methods are compatible with any number of medical instruments, including conventional laparoscopic and endoscopic instruments used in surgical procedures.

There are significant and ongoing developments in the field of minimally invasive surgery, where substantial surgical procedures are conducted with relatively minimal trauma to the patient body. For example, endoscopic procedures access a patient's internal regions via introduction through the patient's mouth to the gastrointestinal region, thereby avoiding a need for an externally located incision. Similarly, laparoscopic procedures access other regions via a relatively small incision through the abdominal wall to the peritoneal cavity. In this manner, endoscopy provides a physician an intraluminal ability to diagnose and treat gastrointestinal (GI) tract abnormalities. In contrast, laparoscopy provides a physician an extraluminal ability to diagnose and treat GI tract abnormalities. Accordingly, there is a need in the art to reliably combine both intraluminal and extraluminal ability in one platform in a manner that is easily used, reliable and robust.

Endoscopic procedures are limited in that the devices must be able to be inserted through the esophagus without causing undue irritation. This, therefore, inherently constrains the number and size of devices that can employed. Furthermore, it can be difficult to reliably control and position multiple endoscopes to specific locations. For these reasons, endoscopic procedures tend to be relatively simple with one endoscope and confined to the upper GI tract, generally the esophagus, stomach and duodenum so as to avoid increasing risk of complications.

Because of the inherent limitations of endoscopic procedures, laparoscopic procedures are also used for introduction of a medical instrument through the abdominal wall, thereby accessing the body extra-luminally. In contrast to an endoscopic procedure where an instrument is introduced through the mouth, laparoscopy requires an opening be made through the abdominal wall for medical instrument access to the inside of the patient, such as the intraperitoneal space. This is typically achieved by using a trocar or other instrument having a sharp distal tip and a passage to provide a working passage for a medical instrument. Those trocars, however, suffer from inherent disadvantages and associated risks. First, the peritoneal membrane must be actively punctured from outside the patient to provide instrument access. This can result in increased risk of infection or other complications. Second, it can be difficult to reliably secure the trocar or other cannula-type element, including for extended periods of time with attendant movements on the trocar from instrument use during the surgical procedure. Lack of a safe, stable, and reliable working channel that traverses the abdominal wall can lead to unwanted complications. Furthermore, current technology requires that if a laparoscopic physician wishes to place a trocar into the gastric lumen via standard laparoscopic technique, they must make multiple abdominal incisions which will allow them to grasp the external wall of the stomach and then fix it to the abdominal wall by multiple suture/staple or other fixation methods. Once the stomach has been fixed in a safe and stable manner, the physician must make an external full thickness incision through the gastric wall and then externally place a surgical trocar that can be used for both passage and manipulation of laparoscopic instruments into the gastric lumen. The trocar must be air-tight to allow air insufflation of the stomach for both internal vision as well as manipulation of instruments. Trocars usually have internal air-tight seals for passage of instruments. The surgeon, however, must ensure an air-tight seal around the external aspect of the trocar to prevent air leakage on an external surface where the trocar contacts the gastric wall. This procedure is complex, with an attendant risk to establish intra-gastric access via laparoscopic surgery, and reflects the inherent difficulty in trocar insertion into a non-solid organ, such as a stomach wall.

For at least these reasons, there is a need in the art for improved abdominal wall ports that provide a work platform through which one or more medical devices are inserted, while avoiding the risks and drawbacks of conventional trocars that are inserted in a direction from the patient skin surface toward and through the peritoneal membrane. In particular, current methods and devices do not allow for an intra-gastric trocar to be placed in a retrograde method which can provide simultaneous access to the lumen of the UGI tract as well as the intra-peritoneal space/organs. The systems provided herein address these problems in a safe, reliable and easy to implement manner, such as by a unique introducer in combination with a cannula that facilitates retrograde introduction to a patient.

SUMMARY OF THE INVENTION

Provided herein is a trans-abdominal gastric surgical system that provides access to a patient's abdominal cavity from outside the patient through the abdominal wall with a uniquely inserted, secured and removable cannula. The unique structure and implementation of the systems described herein provide a number of important functional benefits that increase the likelihood of a successful outcome and minimizes risk of an adverse event. First, the system is readily and easily deployed, with a retrograde introduction from the oral-pharynx, esophagus, to the stomach lumen, and into the abdominal wall, with an internal anchor in contact with an inner-facing surface of the stomach wall or an inner-facing surface of the peritoneal wall such as by following the course of the opening by the guidewire tract through the stomach wall and via the peritoneal space, by a simple pulling force on a guidewire connected to the system that passes through an incision in the abdominal wall. Once in place, the cannula portion is readily anchored through the use of opposed anchors, an internal anchor that is anchored to the gastric or peritoneal surface and an external anchor opposed to the internal anchor that is anchored to the skin surface. This results in an extremely reliable and robust positioning of the cannula, through which a surgeon can access internal regions of a patient, both in an intra-luminal and/or extra-luminal manner. Closure elements may be inserted at the start of the procedure, making system removal and incision closure simple, quick and reliable with an attendant decrease in scarring-related issues, tissue sensitivity, pain, infection and wound re-opening.

The systems are compatible with a wide range of applications including related to the ability to manipulate tissues, provide internal sutures, and accommodate a variety of anastomotic devices. Further advantages include the ability to maintain a desired spatial orientation during a surgical procedure as well as providing the ability to multitask via the introduction of a plurality of medical instruments that do not interfere with each other. If there is an adverse event during a surgical procedure, the systems herein allow for rapid management and mitigation, including any of a number of intraperitoneal complications such as a hemorrhage event. Other advantages include the ability to triangulate on a specific region of interest in either a one-cannula or two-cannula configuration. Furthermore the systems provided herein are compatible with any generic endoscopic or laparoscopic instrument.

The minimally invasive and low complication incidence provided by the instant systems means unwanted physiological events are avoided along with attendant decrease in training efforts and costs, with both improved patient outcomes and decreased healthcare costs. The simplicity and elegance of the systems ensure a rapid learning curve is achieved by a spectrum of caregivers, such as a community gastroenterology physician and surgical physicians.

In an embodiment, provided herein is a trans-abdominal gastric surgical system comprising a cannula. The cannula is a passage that, during use, provides access to the gastric environment. The cannula has an outer end, an inner end, and a central portion having an outer-facing surface that extends between the inner end and the outer end, and an inner-facing surface that defines a lumen configured to receive a portion of a medical instrument that traverses between the outer end and the inner end. An internal anchor is connected to the inner end and has a surface shape configured to secure the system against an interior surface of a gastric wall or peritoneal surface. In this aspect, connected is used broadly to include a single piece of material having a portion defined as an internal anchor from which a cannula extends. Alternatively, the connection may refer to two separate pieces, the cannula and internal anchor, which are permanently or removably connected. An external anchor is removably and translationally connected to the cannula outer-facing surface and has a surface shape configured to secure the system against a skin surface.

Accordingly, in use the system provides two opposed surfaces connected to and securing the cannula to the abdominal wall, with the internal wall securing the system in a direction from the gastric environment to the abdominal wall, and a counter-directed force from the external anchor toward the abdominal wall.

The systems and related methods provided herein is a useful platform for a number of applications. Depending on the application of interest, the system accommodates a medical instrument that extends from outside the body to inside the body, via the cannula passage. Examples of medical instruments include, but are not limited to, laparoscopic and endoscopic instruments for minimally invasive surgery such as for tissue incision, removal, handling, illumination, surgery, suturing, stapling and the like.

In an embodiment, the internal anchor surface shape is adjustable, deployable, or both. Examples include an internal anchor selected from the group consisting of: a balloon; a hinged umbrella; and a flexible bumper. In a more basic implementation, the internal anchor surface does not substantially change shape, but instead is shaped and sized to permit endoscopic introduction from the mouth to the stomach while maintaining the ability to reliably secure the device against an internal-facing surface, such as the gastric wall or a peritoneal surface.

In an aspect, the internal anchor encircles the cannula inner end and is configured to secure the system to an interior surface of a gastric wall or an interior surface of a peritoneal cavity. In an embodiment, the internal anchor comprises a bumper and the bumper and the cannula are formed from a unitary material.

The bumper has a shape to provide reliable contact with a patient's inner-facing surface, including the stomach wall or a peritoneal cavity surface. For example, the curved outer surface may have a maximum diameter that is greater than or equal to 2 cm and less than or equal to 4 cm, a height that is greater than or equal to 0.5 cm and less than or equal to 2.5 cm, an open exit having a diameter that is less than or equal to 3.5 cm; and a hollow interior volume defined by said curved outer surface and through which a medical device can traverse. The hollow interior volume advantageously provides a well-defined space through which a medical device extends, thereby assisting with medical device control and positioning to enhance stability, while minimizing adverse effects on surrounding tissue during medical device insertion and removal and during an extended medical procedure.

Any of the systems provided herein may have an external anchor that comprises a disc having an inner-facing surface that defines a passage for receiving the cannula. In this aspect, the cannula and inner-facing surface may have a circular shape to provide a translational connection by a matched internal thread and external thread pair on facing surfaces of the disc inner-facing surface and the cannula outer-facing surface, wherein rotation of the disc relative to the cannula outer-facing surface translates the disc along at least a portion of the cannula outer-facing surface in a longitudinal direction along the cannula axis. Alternatively, the translational connection may comprise other connections, such as a friction-fit, clamp fit, or set screw fit.

In an aspect, the disc comprises a central body that defines the passage and a flange connected to the central body, the flange comprising a plurality of passages extending there through. The plurality of passages may be arranged in a circumferential offset pattern relative to a central body having a substantially circular shape. Adjacent passages may be separated by a separation distance that is greater than 1 mm and less than 4 mm and have alternating separation distances from the central body corresponding to a minimum separation distance and a maximum separation distance. For example, the minimum separation distance may be less than about 7 mm and the maximum separation distance greater than about 7 mm.

The flange may have an outer edge that comprises a plurality of straight edges, such as an octagon shape and corresponding number of passages. For example, the plurality of passages may number eight, with four corner-positioned passages and four side-positioned passages. Adjacent corners may be separated by an individual side-positioned passage, with the corner-positioned passages separated from the central body by the maximum separation distance and the side-positioned passage separated from the central body by the minimum separation distance. In an aspect, each of the plurality of passages is positioned adjacent to a corner region of the octagon shape flange outer edge. Each of the passages may be positioned within about 1 cm from the edge of the flange. In an aspect, each of the edges that define the flange outer edge has equal lengths. For an octagon embodiment, the edges may have a length that is between about 1 cm and 2 cm and accordingly spaced from an outermost edge of the central body of between about 0.5 cm and 1.5 cm. The maximum length of the disk may be between about 2 cm and 5 cm.

Any of the systems provided herein may further comprise a plurality of suture threads, wherein each individual suture thread traverses a pair of opposed passages, and may loop around an outermost portion of the internal anchor, without adversely impacting any of the one or more medical devices extending there through. For example, the suture threads may be positioned at the start of a procedure, the procedure performed, medical devices removed, and the suture threads pulled to remove the system from the patient and to reliably close an incision, as explained hereinbelow In an aspect, the internal anchor is configured to ensure the internal anchor does not touch or otherwise interfere with suture placement. In this manner, placed suture threads do not adversely interfere with medical instruments that are introduced via the cannula and are, for example, moving in and out relative to the internal anchor, while still being ready to be engaged when the procedure is completed and the wall incision is to be closed.

Any of the systems provided herein may further comprise a cap removably connected to the cannula outer end. Such a cap is useful to providing an air-tight passage for introduction of medical instruments through the cannula from outside a patient so that a distal end of the medical instrument is provided inside the patient and extending past the internal anchor.

The cap may comprise one or more instrument ports configured for introducing one or more medical instruments to the cannula lumen and out of the inner end and into a patient when the system is anchored to a gastric wall or a peritoneal surface by the internal anchor and a skin surface by the external anchor.

The cap may comprise a plurality of instrument ports formed from a memory sealant, each instrument port having an independently selected size and introduction angle. The memory sealant may be a shape memory polymer. The memory sealant may be formed from a single layer or a multilayer. In such a manner, upon removal of the medical instrument, the memory sealant may form an airtight seal between the external and internal side of the sealant.

In an aspect, any of the systems may further comprise a pressure port operably connected to the cap for measuring or controlling pressure at the cannula inner end. In this manner, the gastric environment and/or intra-peritoneal spaces may be pressurized to a desired pressure, such as to improve access, improve field of view, or otherwise prepare the patient for a medical procedure.

In an aspect, any of the systems may further comprise a stopcock connected to the cap for providing controlled access to the cannula lumen.

Any of the systems provided herein may also be configured for introduction or insertion into the gastric lumen, such as by a retrograde introduction to the stomach from the esophagus. Accordingly, the system may have an external anchor removed configuration for the external anchor removed from the cannula. In this aspect, the system may further comprise an introducer removably connected to the cannula outer end in the external anchor removed configuration. Such external anchor removal may ready the system for insertion into a patient.

In this aspect, the introducer may comprise a receiving opening that removably receives the cannula outer end and at least a portion of said cannula central portion. The connection may be equivalent to the connection employed with the cap-cannula connection or external anchor-cannula connection, such as a threaded connection.

In an embodiment, the introducer comprises a distal end; a proximal end through which the receiving opening traverses; a tapered central portion extending between the distal end and the proximal end; a capture element connected to the distal end; and wherein the tapered central portion is configured for introducing the system to a patient by retrograde introduction past a patient's oropharynx by pulling a guidewire connected to the capture element in a direction away from the introducer connected to the system.

In an embodiment, the introducer and cannula have a flexibility or bending moment selected so that the introducer is capable of deforming to follow contours of a patient oral-pharynx and esophagus during insertion in a patient. For example, the material hardness or durometer may be selected to ensure device insertion via a retrograde direction without undue adverse patient impact. Preferably, the material is a soft durometer plastic, polymer or elastomeric material.

Once the introducer is pulled through the guidewire insertion region, the introducer is removed to provide a system having an introducer removed configuration. The system in an introducer removed configuration is then ready to receive an external anchor that is connected to the cannula outer surface in an external anchor deployed configuration.

In another embodiment, the invention is an insertable trans-abdominal gastric surgical system comprising an introducer having a receiving passage and an outer tapered surface; a cannula having an outer end removably connected to the introducer receiving passage; an inner end; and a central portion having an outer-facing surface that extends between the outer end and the inner end and an inner-facing surface that defines a lumen configured to receive a portion of a medical instrument that traverses between the outer end and the inner end. An internal anchor is connected to the inner end and has a surface shape configured to secure the system against an interior surface of a gastric wall or peritoneal surface. The introducer, cannula and internal anchor are configured for insertion to a patient's gastric lumen by retrograde introduction past a patient's oropharynx, along an esophagus, and into the stomach lumen.

Any of the systems provided herein may have an introducer that comprises a distal end; a proximal end through which the receiving passage traverses, wherein the receiving passage has an at least partially threaded inner-facing surface to rotationally and removably engage an at least partially threaded cannula outer facing surface.

Any of the systems provided herein may have an introducer further comprising a capture element connected to the distal end configured to connect to a guidewire to facilitate guided insertion in a direction through a patient's oropharynx, esophagus, stomach and abdominal wall, such as by a pulling action of the guidewire that is connected to the capture element away from the system. In this manner, the capture element then transmits the pulling action to the rest of the system, thereby moving the entire system.

In an aspect, the introducer may be further described in terms of the outer tapered surface having: an angle of incidence at the distal end that is greater than or equal to 5° and less than or equal to 20°; a total length that is greater than or equal to 2 cm and less than or equal to 15 cm; a tapered portion extending from the distal end and a substantially untapered portion extending between the proximal end and the tapered portion, having a tapered portion longitudinal length to untapered portion longitudinal length ratio ($L_T/L_U$) that is greater than or equal to 1 and less than or equal to 5; and wherein the introducer has a flexibility selected so that said introducer is capable of deforming to follow contours of a patient's oral-pharynx and esophagus during insertion into a patient.

In an aspect, the cannula portion of the system may be further described in terms of certain dimensions, such as length and diameter. For example, the cannula length may be between 4 cm and 30 cm, and any sub-ranges thereof, such as between 6 cm and 10 cm. The cannula diameter may be selected from a range of between 5 mm and 70 mm, including a diameter that is greater than or equal to 5 mm and less than or equal to 20 mm, and any sub-ranges thereof. The introducer diameter may be accordingly sized to match the cannula diameter, such as a diameter of between 5 mm and 70 mm, or between 5 mm and 20 mm, and any sub-ranges thereof.

The introducer and/or cannula may be made from a material having a desired durometer, rigidity and flexibility, such as medical grade silicone, polyvinyl chloride (PVC), plastic, rubber, or other material known in the art of medical devices and implants.

Also provided are various methods related to any of the systems described herein. In an embodiment, provided is a method of inserting a trans-abdominal gastric surgical system in a patient by inserting a guidewire through an abdominal wall insertion and into a stomach lumen; guiding a portion of the inserted guidewire out of the stomach lumen, through an esophagus and mouth to provide an accessible portion of the guidewire; connecting a capture element of an introducer trans-abdominal gastric surgical system assembly to the accessible portion of the guidewire; pulling the guidewire connected to the capture element of the introducer trans-abdominal gastric surgical assembly in a direction away from the patient so the assembly is introduced thru the oral-pharynx and esophagus into the stomach lumen; advancing the introducer portion of the assembly out of the stomach through the abdominal wall incision so that an internal anchor of the trans-abdominal gastric surgical system contacts an inner-facing surface of the stomach; removing the introducer from the assembly to reveal an exposed end of trans-abdominal gastric surgical system; removing the guidewire; connecting an external anchor to the exposed end of the trans-abdominal gastric surgical system; and moving the external anchor in a direction toward a skin surface of the patient to reliably secure the trans-abdominal gastric surgical system to the patient. In this manner, the trans-abdominal gastric surgical system is inserted and reliably secured to the abdominal wall of the patient.

In an aspect, the method further comprises the step of attaching a cap to the exposed end of the inserted trans-abdominal gastric surgical system. Alternatively, the system may be configured to have a self-contained cap over which the introducer extends, so that upon removal of the introducer, the cap is revealed.

The method is further useful for a variety of surgical procedures, including a procedure on a human or a non-human animal. For example, the method may further comprise the step of introducing one or more than one surgical instruments through the trans-abdominal gastric surgical system for use in a procedure selected from the group consisting of: instrument triangulation; accessing a stomach lumen; accessing a retroperitoneal space; manipulating tissue; closing an incision; a gastric surgery; a gall bladder surgery; single or simultaneous access to an upper GI tract and small intestinal lumen; access of an intra-peritoneal space and its associated organs, such as the stomach wall, liver, gall bladder, colon; and access of an extra-peritoneal or retro-peritoneal space and associated organs, such as spine, pancreas, kidney, or any combination thereof.

In an aspect, any of the methods further comprise the step of removing the trans-abdominal gastric surgical system after procedure completion in a reliable, simple and robust manner that minimizes post-operative discomfort or complications. The removal may comprise inserting at a start of or before the procedure a plurality of sutures by: introducing a cannulated-introducer needle through a first passage in the external anchor and through a first underlying tissue region comprising an abdominal and gastric wall and into a gastric environment, either for a single-layer closure or in a repeated manner for multiple-layer closure; introducing a suture grasper through a second passage in the external anchor and through a second underlying tissue region comprising the abdominal and gastric wall and into the gastric environment, wherein the second passage is opposably positioned relative to the first passage; placing a suture thread proximal portion through the cannulated-introducer needle; guiding a suture thread distal portion around and away from the outer-facing surface of the internal anchor to ensure there is no interference by the thread on movement and use of a medical instrument passing therethrough, wherein the suture thread distal portion longitudinally extends from the suture thread proximal portion; grasping at least a portion of the suture thread distal portion with the suture grasper; pulling the suture grasper and suture thread distal portion out of the gastric environment and through the underlying abdominal and gastric wall and the external anchor second passage wherein the suture thread portion in the body is positioned around or beyond said internal anchor to avoid interference with an instrument introduced through a working channel formed by the trans-abdominal gastric surgical system, and securing the suture ends outside the body to ensure the suture thread ends are not pulled back into the patient, such as by clamps that lay externally to the patient, thereby providing a reliable pre-closure suture; repeating the above steps with a second suture thread positioned through a third external anchor passage, fourth external anchor passage, and corresponding third and fourth underlying tissue regions comprising the abdominal and gastric wall; optionally, the steps are repeated with a third suture thread and fifth and sixth external anchor passages, as desired and depending on the number of available external anchor passages. The cannulated-introducer needle and the suture grasper are removed to reveal matched pairs of suture thread proximal and distal portions that extend out past the external anchor outside the patient skin surface; the external anchor is loosened or optionally removed from the exposed end of the trans-abdominal gastric surgical system; the revealed matched pairs of suture thread proximal and distal portions are pulled in a direction away from the patient, thereby removing the trans-abdominal gastric surgical system from the patient; and closing the incision by suturing the suture threads in a position that is outside the abdominal wall thereby closing abdominal wall incision.

Any of the devices described herein may be introduced at other locations, as desired. For example, the trans-abdominal surgical system may be temporarily positioned with an internal anchor in the gastric lumen, and a distal portion in the peritoneal cavity that is on the other side of the gastric wall. In this temporary position, prepositioned sutures may be placed through the gastric wall and secured, and the system then pulled externally so as to force the internal anchor through the gastric wall, leaving behind an opening in the gastric wall, but having prepositioned sutures that can be used to efficiently close the incision at a later time and in alignment with a corresponding incision through the abdominal wall, such as upon procedure completion. The system may be continued to be pulled so that the internal anchor rests against the peritoneal surface and an external anchor may be positioned to secure the system against the patient skin surface. In this manner, the system internal anchor is anchored to the peritoneal surface, instead of the gastric wall, with an opening in the gastric wall that may be used to pass a scope and/or other instruments into the peritoneal space from the gastric lumen for any of a multitude of procedures. This then, provides the capability of having a second transabdominal gastric system having an internal anchor opening that is extraluminal relative to the stomach.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 10. Cross-section of the system through the first and second external anchor flange passages to illustrate suture thread introduction.

DETAILED DESCRIPTION OF THE INVENTION

Figure 1A:
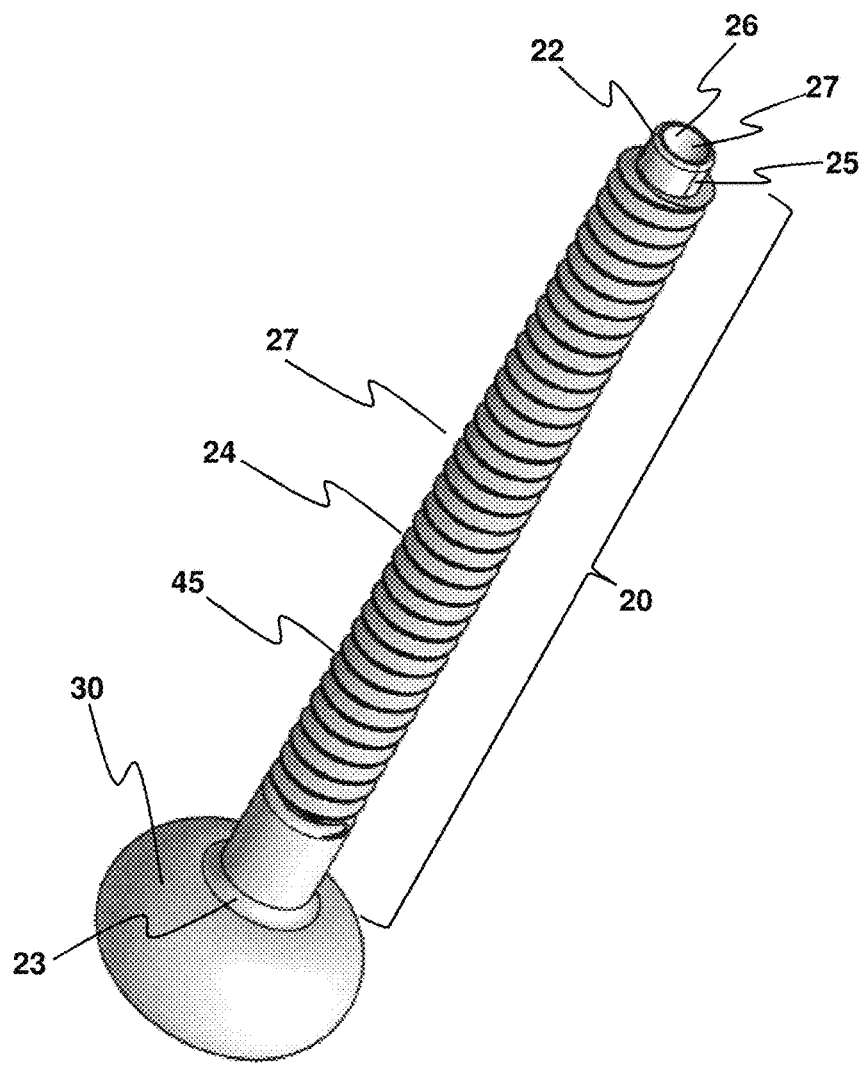
FIG. 1A. Perspective view of a trans-abdominal gastric surgical system without an external anchor.

In general, the terms and phrases used herein have their art-recognized meaning, which can be found by reference to standard texts, journal references and contexts known to those skilled in the art. The following definitions are provided to clarify their specific use in the context of the invention.

"Bumper" refers to a shape of the internal anchor outer surface that is substantially curved and configured to provide reliable contact with an inner surface of a biological tissue, such as the stomach wall or peritoneal surface.

An "internal anchor" of the present invention is the element that is positioned in the body and that anchors the device to an inner surface of the body, in combination with the external anchor. The internal anchor may be shaped and configured so as to facilitate controlled transit through an incision in a wall, such as a gastric and/or an abdominal wall. For example, the internal anchor may be a relatively thin-walled bumper shaped to provide an exit volume on an inner-facing surface with the outer-facing surface providing a reliable connection to a luminal-facing surface of a wall, such as a gastric wall, a peritoneal wall, or an abdominal wall. In this manner the bumper may secure the system to a wall under a securing force. As desired, a removal force that is greater than the securing force may be used to controllably pull the internal anchor through the gastric wall and/or abdominal wall. "Adjustable" or "deployable" internal anchor surface shape refers to an internal anchor that can be adjusted or actuated from a first state or shape to a second state or shape. For example, a balloon-type internal anchor can have a surface shape that is adjustable by varying the pressure in the internal volume encompassed by the balloon surface or deployable by inflating from an uninflated state. An umbrella-type mechanism may be adjusted to provide surface shape adjustability in curvature. This aspect also facilitates control of the total surface contact area between the internal anchor surface and the corresponding biological surface, including the stomach or peritoneal wall.

"Flexible" refers to shape deformation under an applied force. Accordingly, a flexible anchor or flexible bumper refers to an anchor or bumper whose shape can at least partially conform to increase the magnitude and reliability of the contact area between the anchor and the corresponding biological surface. A flexible introducer, refers to the ability to deform in order to navigate the contour of a patient's anatomy for system introduction. One quantitative indication of flexibility is Young's modulus (defined as stress/strain). In an aspect, the introducer and/or cannula is formed of a polymer material having a Young's modulus that is less than or equal to 10 GPa, less than or equal to 10 MPa, or less than about 1 MPa, or any other range that provides the desired functional outcome of system flexibility during introduction along the esophagus. Similarly, the material durometer is selected to ensure the system and cannula is relatively soft to further reduce irritation during introduction or passage through a biological tissue.

Similarly, the dimensions and geometry of the introducer and cannula in combination with the material properties may provide a bending moment useful for system introduction to the gastric environment via the esophagus. "Bending moment" refers to the force on a portion of the introducer and cannula that generates a corresponding deflection of the introducer and cannula. The bending moment may be quantified based on a cantilever approximation, with an introducer having one end fixed, such as the proximal end that is connected to the cannula, and the other end such as the distal end that is free to move. The bending moment is selected so that a typical force experienced when introducing the system into a patient allows the system to follow contours of the oral-pharynx and esophagus, the system correspondingly bends or deflects to follow the contours and facilitate introduction and minimize unwanted forces on the oral-pharynx and esophageal wall.

"Removably connected" refers to a configuration of elements, wherein the elements can be temporarily connected to each other and, as desired, removed from each other without adversely impacting the functionality of other elements of the device. "Translationally connected" refers to a configuration of elements, wherein motion of one element is substantially unidirectional and parallel with respect to another element, wherein movement of one element does not affect each element's functionality. "Operably connected" refers to a configuration of elements, wherein an action or reaction of one element affects another element, but in a manner that preserves each element's functionality. For example, a pressure port operably connected to a cap refers to the ability to monitor or effect pressure change without impacting the functionality of the cap, including having other ports for introduction of medical instruments.

"Unitary material" refers to two elements that are integrally connected, such as an internal anchor and cannula that are formed from one piece. This is in contrast to identical material that may have separate elements that permanently connected, such as by an adhesive or bond, or removably connected such as by a threaded connection.

"Capture element" refers to the portion of the introducer on which a force is exerted so as to advance the system into the patient, such as past the oropharynx, down the esophagus, into the gastric environment and through the abdominal wall so that one end of the system remains in the patient and the opposite end is accessible from the environment that is outside a patient's body. The invention is compatible with a range of capture elements, so long as the ability to reliably introduce the system by retrograde introduction via the esophagus is not impacted. Specific examples include, but are not limited to, a wire loop, a suture, a connection mechanism such as snap-fit, magnets, threaded attachment, clamp or fasteners.

"Fluid" refers to a material that may be removed or introduced from a volume to effect a change in pressure, including a material that flows under an applied force. Depending on the application of interest, the fluid may be a gas, a liquid, a gel, or a combination thereof.

Unless defined otherwise, "substantially" refers to a value that is within at least 20%, within at least 10%, or within at least 5% of a desired or true value. Substantially, accordingly, includes a value that matches a desired value.

Example 1: Trans-Abdominal Gastric Surgical System

Figure 10:
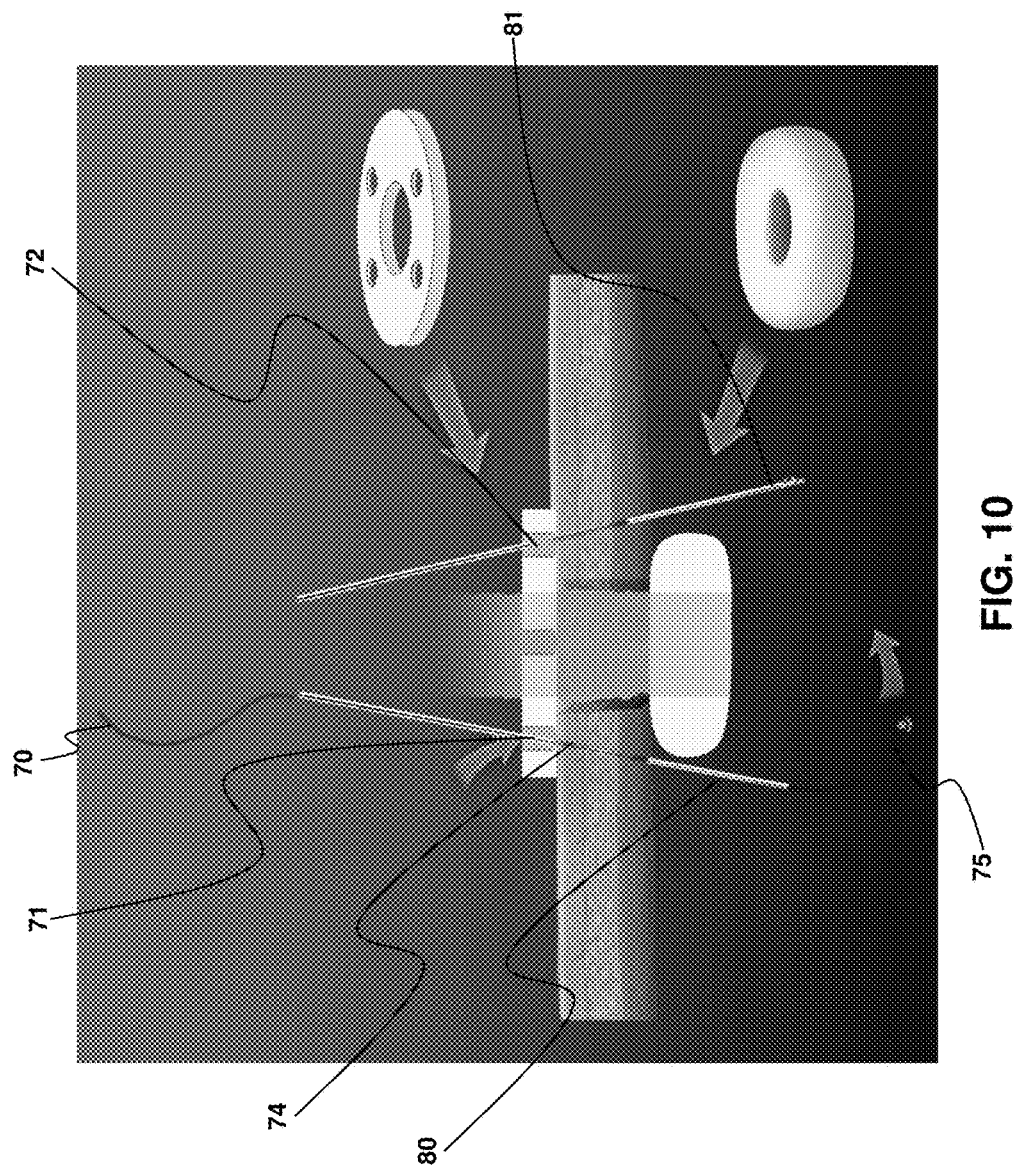

Referring to FIGS. 1-3, a trans-abdominal gastric surgical system, also interchangeably herein as trans-abdominal gastric cannula 10 or generally, system, has a cannula 20 with an outer end 22, an inner end 23 and a central portion 24. Central portion has an outer-facing surface 25 that extends between the inner end and the outer end and an inner-facing surface 26 that defines a lumen 27 configured to receive a portion of a medical instrument 12 (see, e.g., FIG. 24) that traverses between the cannula outer and inner ends, such as from outside the patient to inside the patient. An internal anchor 30 is connected to the inner end 23 and has a surface shape 32 configured to secure the system against an interior surface of a gastric wall or peritoneal surface. An external anchor 40 is removably and translationally connected to the cannula outer-facing surface and has a surface shape 42 configured to secure the system against a skin surface (FIGS. 10-1F). Accordingly, FIGS. 1A-1C illustrates an external anchor removed configuration, because external anchor 40 is not connected. This is in contrast to FIGS. 10-1F and FIGS. 2A-2D (also showing cap 50), where external anchor 40 is connected and is capable of being positioned at various longitudinal distances along cannula axis, as indicated by arrow 46 directed along the system longitudinal axis.

Figure 2A:
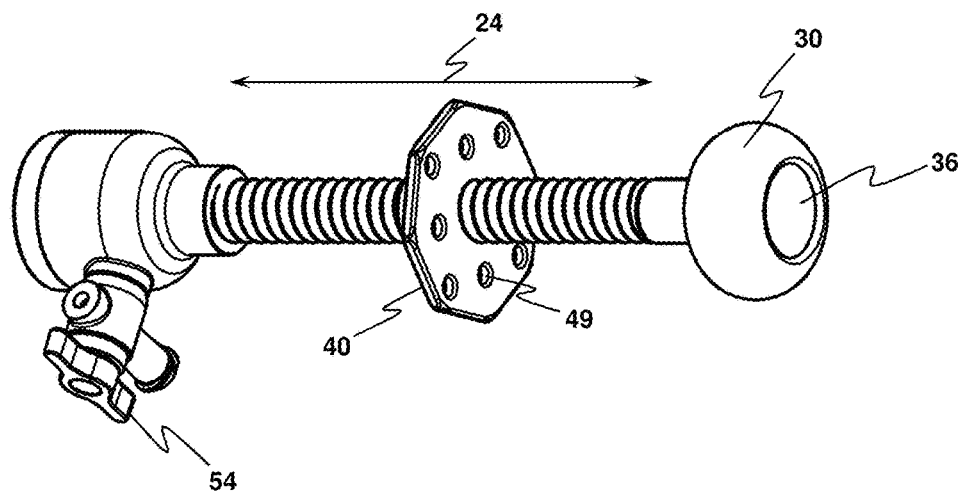
FIGS. 2A-2D. Views of a trans-abdominal gastric surgical system with external anchor and cap showing the interior volume of the internal anchor (FIG. 2A), the instrument port (FIG. 2B), a side view (FIG. 2C) and cross-section showing internal surfaces (FIG. 2D).
Figure 2B:
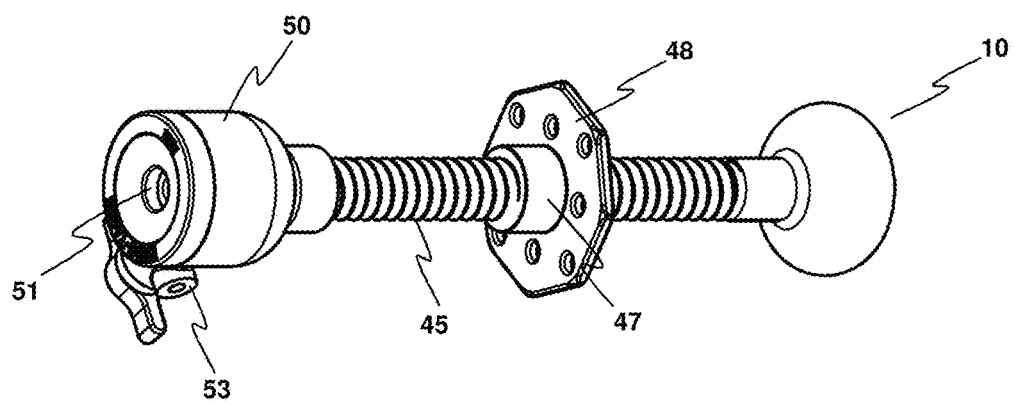
Figure 2C:
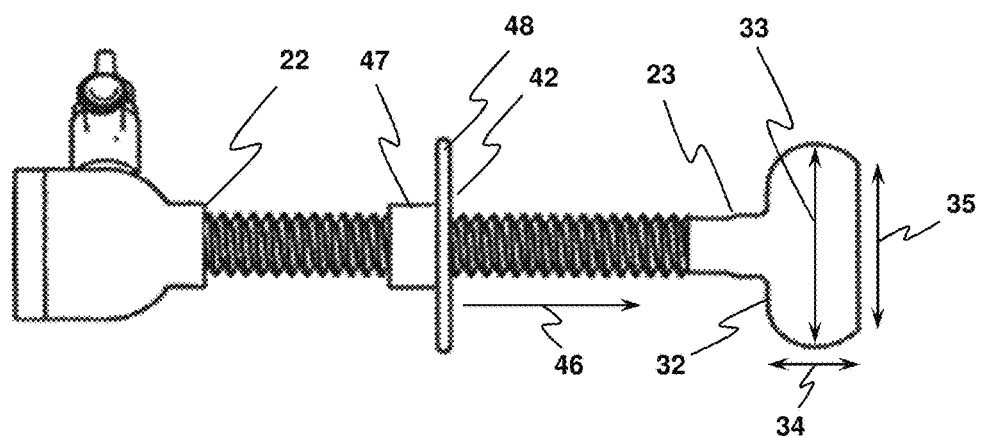
Figure 2D:
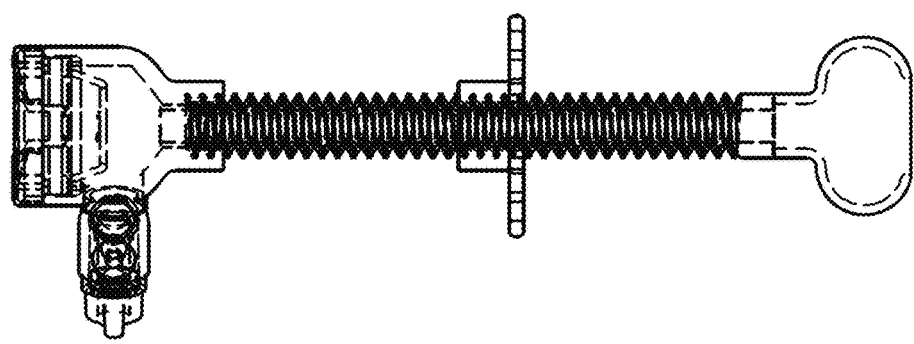

As illustrated, the internal anchor may correspond to a bumper having a curved outer surface 32 with a maximum diameter 33, a height 34, an open exit diameter 35, and a hollow interior volume 36 formed by a thin-wall 37 (see, e.g., FIG. 1B-1C and FIG. 2C).

Figure 1F:
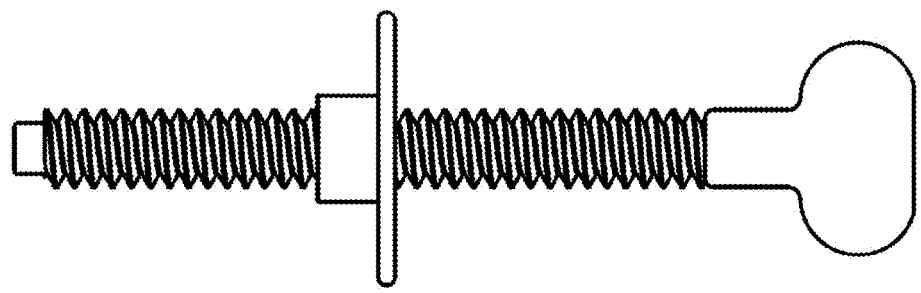
FIGS. 10-1F are perspective views of the system in an external-anchor connected configuration.
Figure 1E:
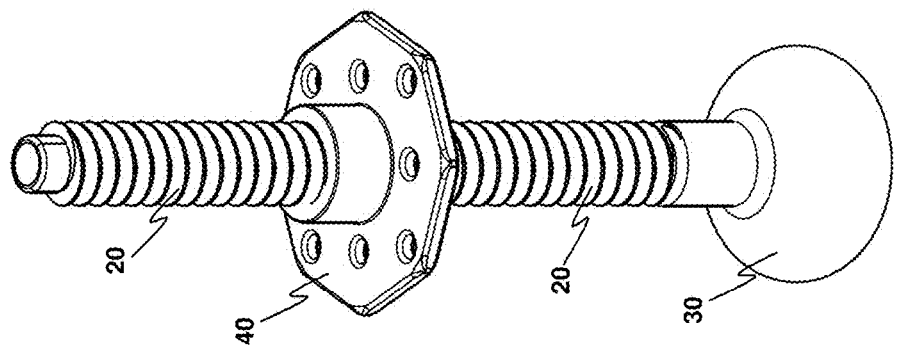
FIG. 1B is a side view of FIG. 1A, illustrating the internal anchor interior surface that forms a hollow opening by the dashed lines.
FIG. 1C is a different perspective view that better illustrates the internal anchor geometry and hollow interior volume.
Figure 1D:
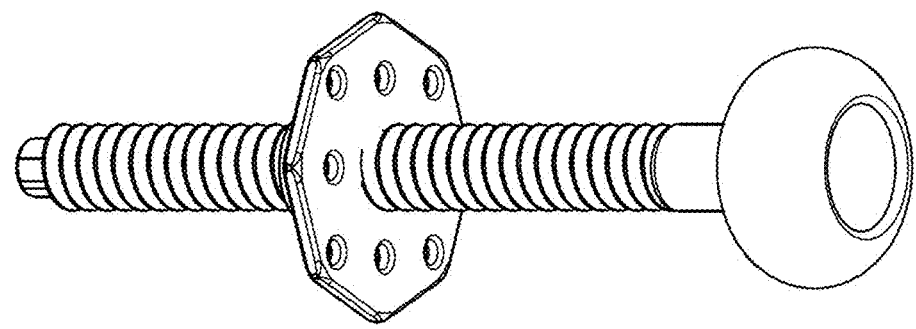
Figure 19:
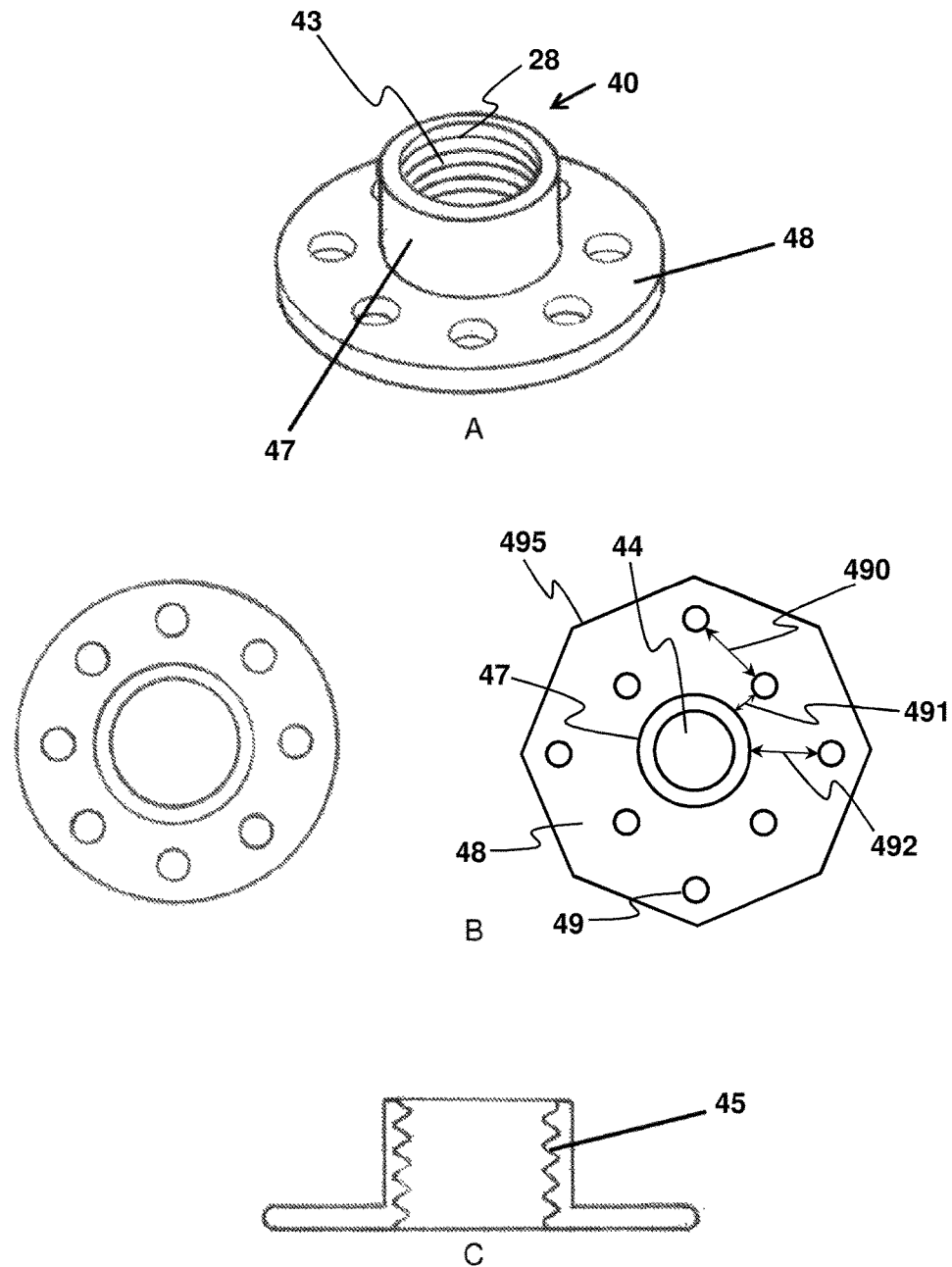
FIG. 19 illustrates an external anchor: A perspective, B top, and C side views. The right panel in view B has an octagon flange edge shape compared to the circular flange edge shape in the left panel.

Referring to FIGS. 1D-1F (external anchor connected configuration), FIGS. 2A-2D (external anchor and cap connected) and FIG. 19 (external anchor removed), external anchor 40 may be a disc having an inner-facing surface 43 that defines a passage 44 for receiving a cannula, more specifically cannula central portion 24. The translational connection between external anchor 40 and cannula 20 may be a matched internal thread 28 and external thread 45, illustrated as being on the inner-facing surface 43 of external anchor 40 and outer-facing cannula surface 25 of cannula 20, respectively. In this manner, the external anchor may be positioned to have any desired separation distance from the internal anchor by moving along the cannula in a longitudinal direction, as indicated by arrow 46. Other translational connections may be employed, including a tight friction fit, clamp, snap-fit, fasteners, set screws, or the like. The external anchor 40 may have a central body 47 in which the passage 44 is disposed and a flange 48 connected thereto. A plurality of second passages 49 may extend through the flange, for facilitating suture placement and system removal.

To provide controlled access to the cannula from the outer end 23 a cap 50 may be removably connected to the cannula outer end (FIG. 2A-2D). The cap may have one or more instrument ports 51 through which one or more medical instruments 12 may be inserted. The instrument port 51 may be formed from a memory sealant material 52, including a multilayer sealant (FIG. 21A). A pressure port 53 may be connected to the cap 50 to control pressure, such as by removal or introduction of a fluid to cannula inner end 22, and thereby to the gastric environment. Controlled access to the cannula may also be provided by a stop-cock 54 type mechanism connected to the cap.

Example 2: Introducer for Introducing the Device to a Patient

Figure 3A:
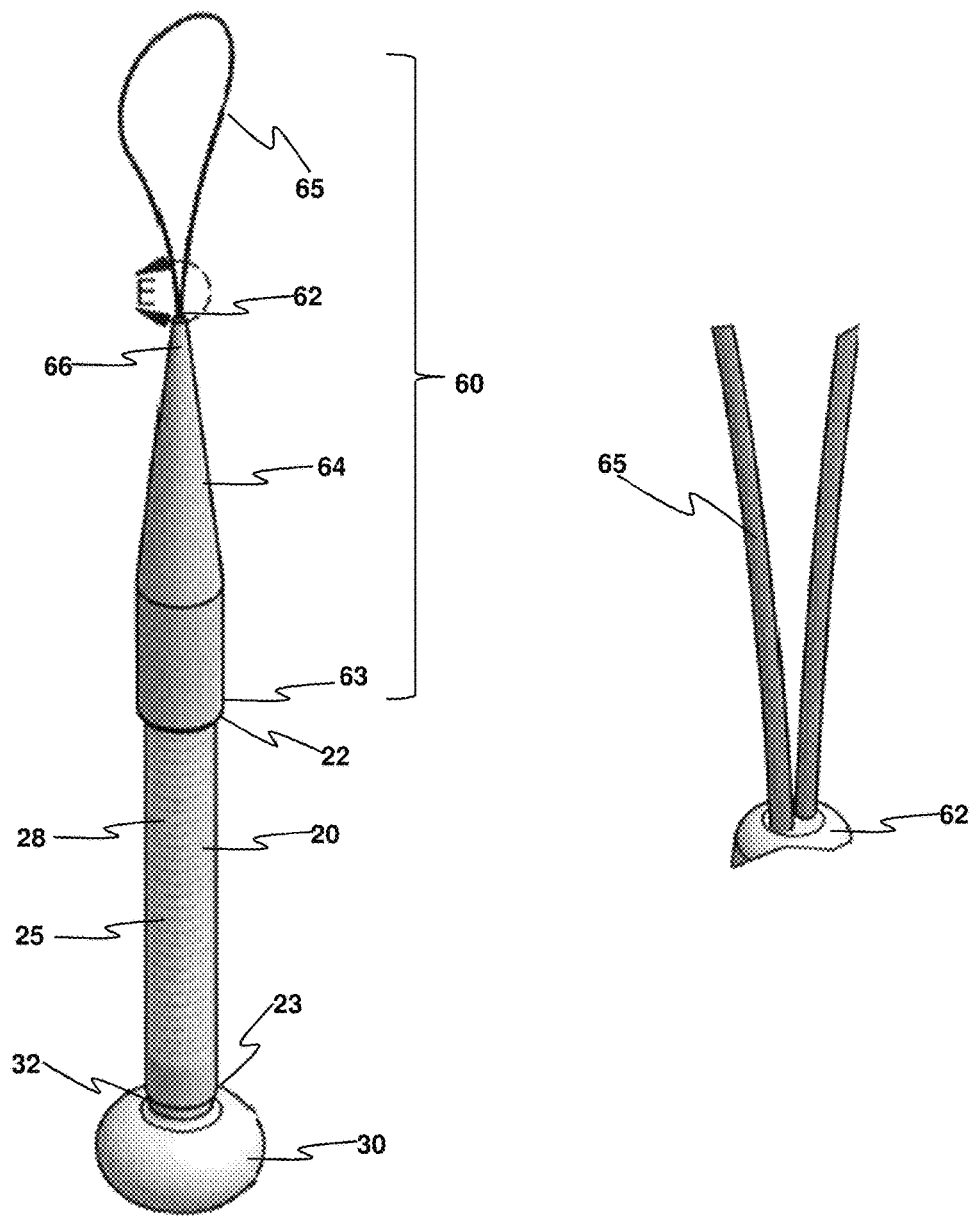
FIG. 3A. A trans-abdominal gastric surgical system and connector element ready to receive a guidewire for insertion into a patient (left panel). The right panel is a close-up view of the capture element connected to the introducer distal end.
Figure 3B:
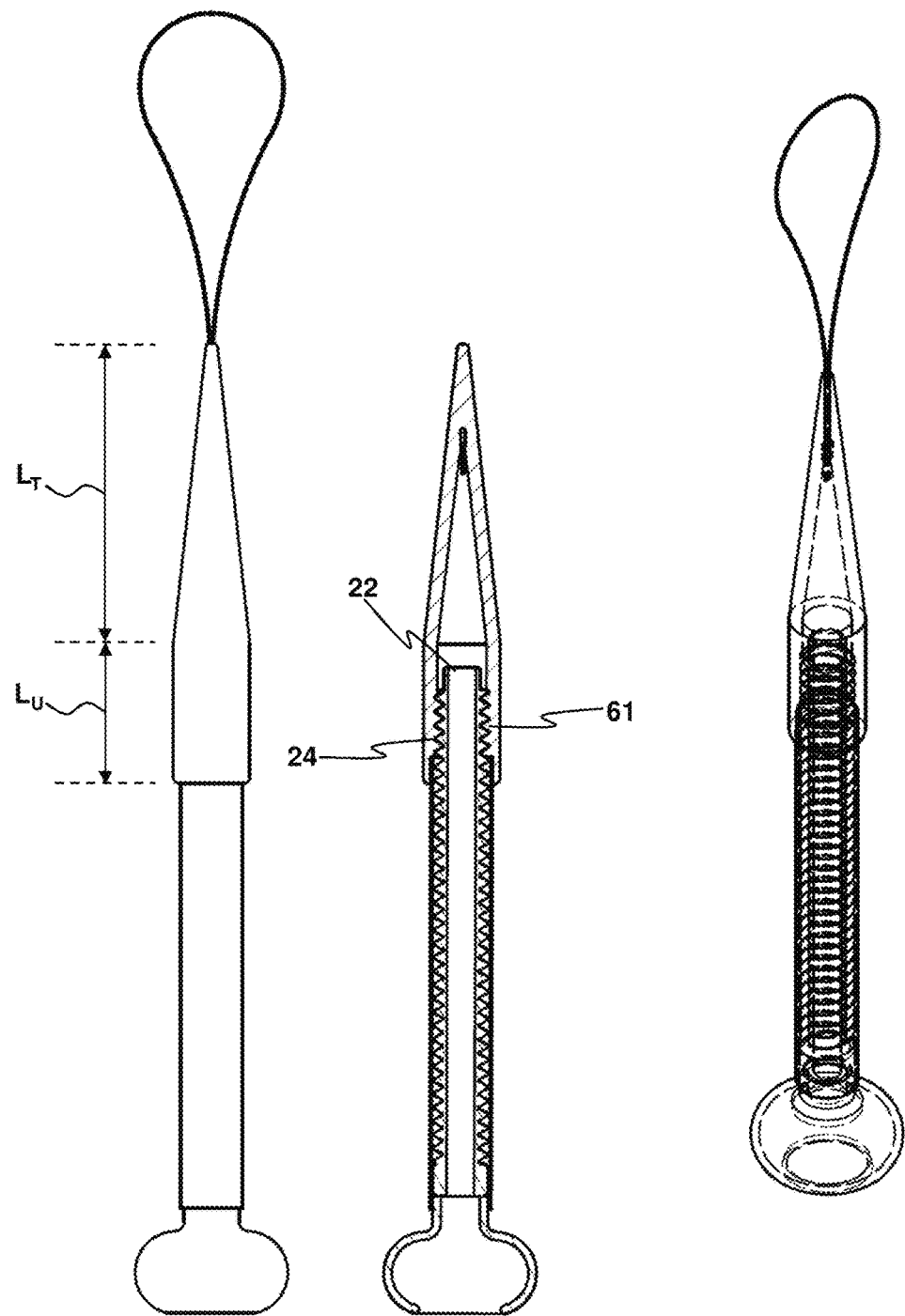
FIG. 3B shows the introducer connected to the trans-abdominal gastric surgical system with a side view with (left panel) and without (middle panel) the capture element, and a perspective view showing the internal surfaces (right panel).
Figure 3C:
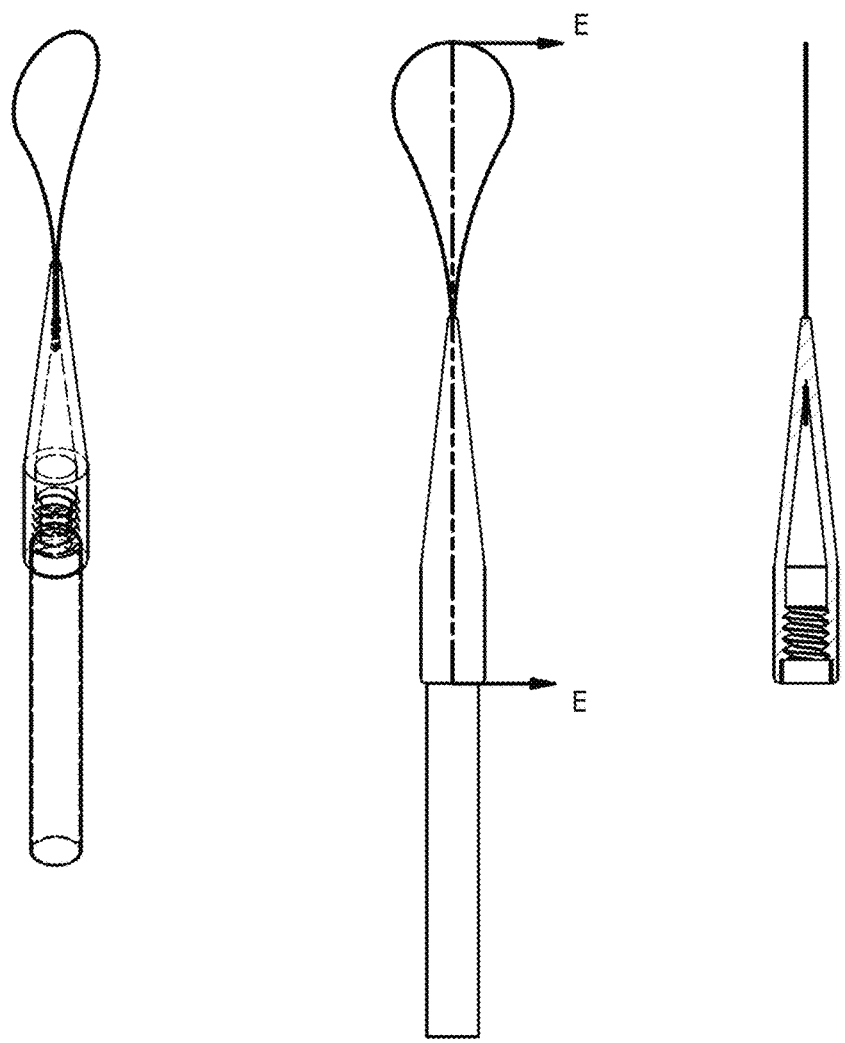
FIG. 3C shows the introducer portion only from a perspective view (left panel), a side view (middle panel) and through cross-sectional line E-E (right panel).

To facilitate system introduction to a patient, an introducer 60 may be used. Referring to FIG. 3A-3C, introducer 60 is removably connected to the system, such as when the external anchor 40 is removed as shown in FIG. 1A-1C, so as to provide a system that may be introduced to the gastric environment by retrograde introduction past a patient's oropharynx and into the gastric environment. Accordingly, FIG. 1A-1C may be further described as in an introducer-removed configuration and FIG. 3A-3B in an introduction ready configuration that is ready to be inserted into the patient by retrograde introduction. The introducer may have a receiving opening 61 that removably receives the cannula outer end 22 and a portion of the cannula central portion 24. The introducer may have a tapered portion longitudinal length ($L_T$) and an untapered portion longitudinal length ($L_U$) and a corresponding ratio, $L_T/L_U$. The receiving passage may have a threaded portion, such as to removably engage with the cannula central portion, in a manner similar to that of the external anchor and cannula central portion. A distal end 62 may connect to a capture element 65, illustrated as a wire loop. A proximal end 63 may contain the receiving opening 61, and a tapered central portion 64 that extends between the distal 62 and proximal 63 ends. In this manner, a guidewire 68 (see, e.g., FIGS. 5-7) may be used to pull the introducer and system combination into the gastric environment. The tapered end of the introducer may then be pulled through the incision in the gastric wall and abdominal wall through which the guidewire passes to provide a reliable contact area between the internal anchor and the gastric wall, as well as gently expanding the abdominal opening to ensure a good fit in the abdominal wall. Similarly, reliable contact area between the internal anchor and an inner facing surface of the peritoneal cavity may be established for an equivalent incision for a guidewire provided therein.

Figure 8:
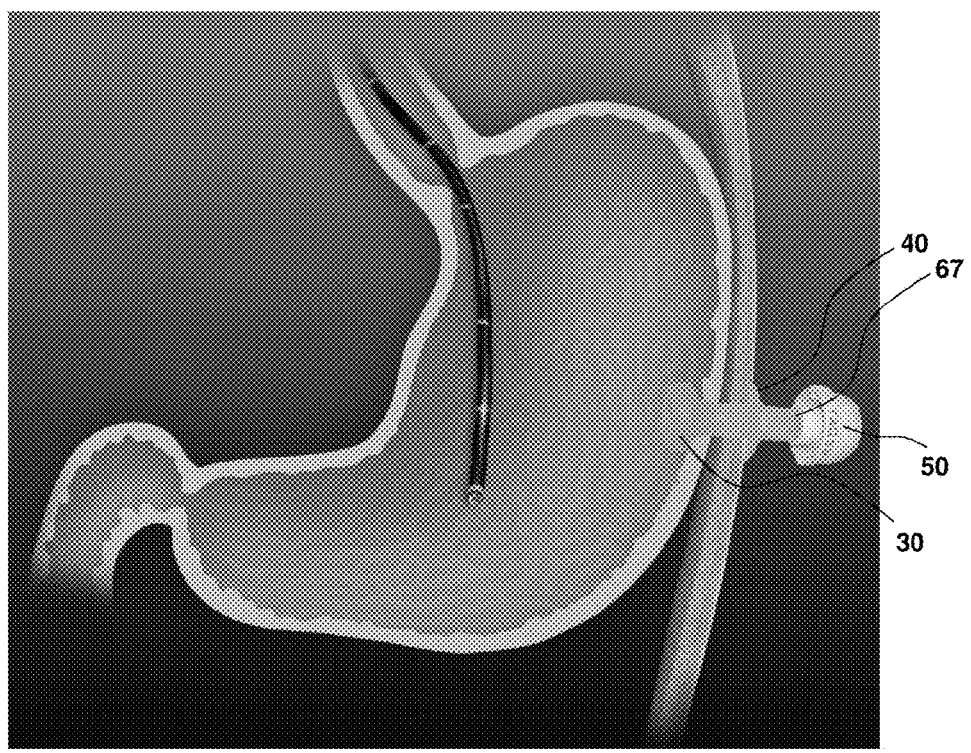
FIG. 8. Internal anchor in position against the gastric wall, introducer removed, external anchor and cap connected, and positioning of the external anchor against an outer surface of the patient to provide reliable positioning of the system and a reliable working channel through the abdominal wall and the gastric lumen. Also illustrated is an endoscope having a fiber optic light source.

Once the system is positioned accordingly, the introducer may be removed to provide an introducer-removed configuration 67 that is ready to receive the external anchor 40, and illustrated in FIG. 8 as having already received external anchor 40 and cap 50 affixed thereto that in combination with internal anchor 30 secures the cannula to the abdominal wall.

Example 3: Closure System Removal

An important benefit of the instant systems and methods is the ability to simply, reliably and robustly close the gastric and abdominal incision or defect through which the system traverses and is pulled through. This is achieved, in part, by the plurality of passages 49 through the flange 48 of the external anchor 40 (FIGS. 2A-2B). Referring to the flow chart of FIG. 9 and corresponding diagrams of FIGS. 10-13 and schematic of FIG. 20, passages 49 facilitate guided insertion and removal of one or more suture threads 70 76 (FIG. 12). In particular, first thread 70 is inserted into first passage 71, such as by a cannulated-introducer needle 80 containing a suture thread proximal portion 74. A suture grasper 81 grabs a suture thread distal portion 75 and pulls the suture thread through second passage 72, that is geometrically opposed to first passage 71. "Geometrically opposed" in this aspect refers to a pair of passages wherein at least a portion of the external anchor central body 47 is disposed therebetween. Accordingly, with the illustrated configuration, the opposed passages may be 180° opposed (see inset of FIG. 13). The invention, however, is compatible with variations on the opposed configuration, so long as a portion of the suture thread traverses the outer-most facing surface of the internal anchor. As desired, a second suture thread 76 is similarly placed through third passage 77 and fourth passage 78 (FIG. 12 inset). In this manner, when the system is desired to be removed, the exposed suture threads are pulled away from the patient to remove the system and provide reliably sutures 82 that close the incision outside the abdominal wall. As desired, for a plurality of unique suture threads, different color threads are used to ensure the appropriate ends are tied together, such as red-to-red and blue-to-blue.

Example 4: System Introduction and Placement

Figure 4:
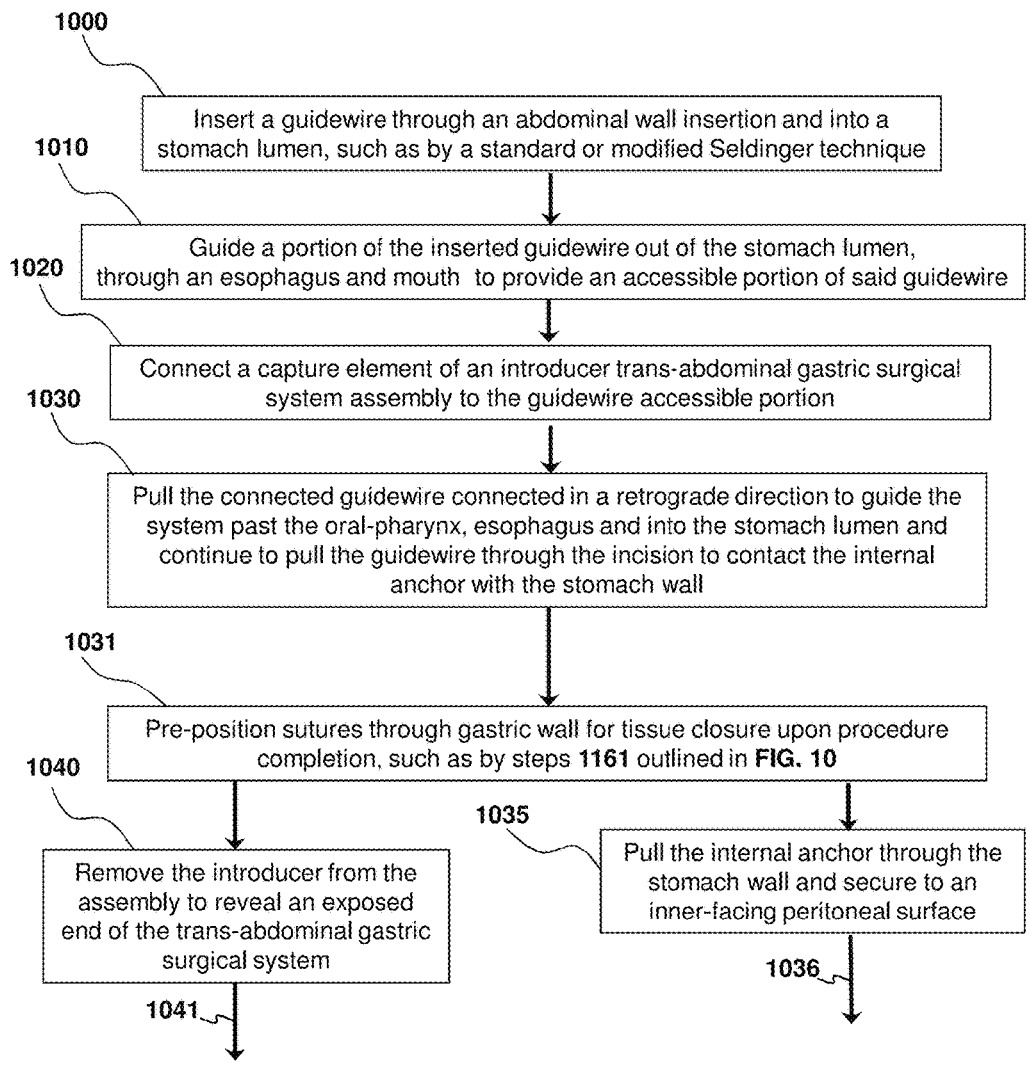
FIG. 4. Flow chart summary of system introduction to a patient and corresponding to illustrations in FIGS. 5-7 for an insertion method to form a working channel to the stomach lumen and FIG. 24 (element 10A providing a working channel to the peritoneal cavity for medical instrument 12A).
Figure 4:
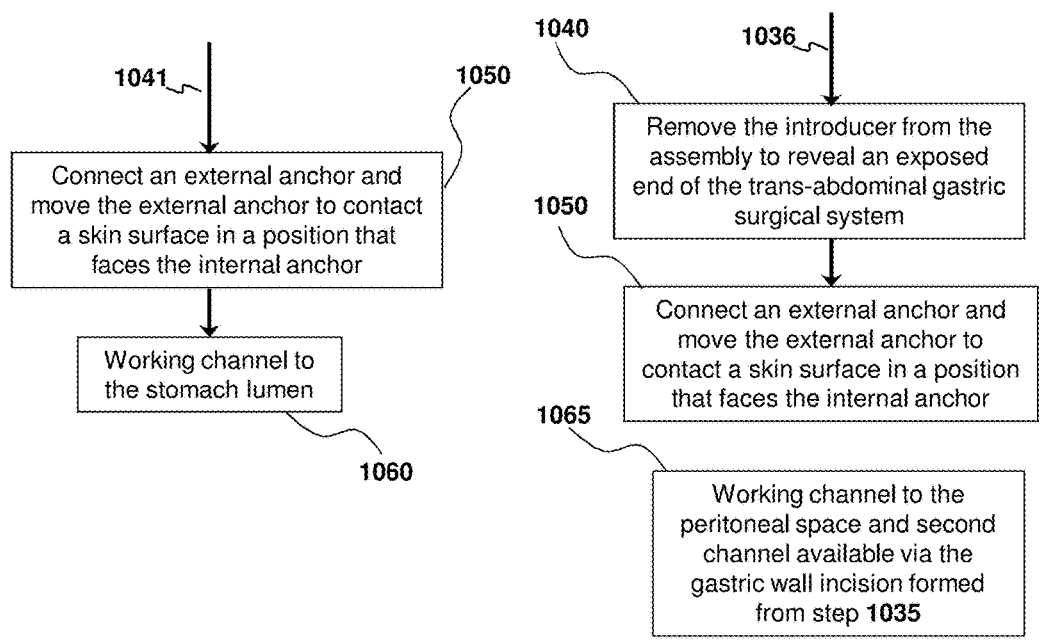

Any one or more of the systems described herein is readily and reliably introduced to a patient. An example of one such method for introducing the system is summarized in the flow chart of FIG. 4 and corresponding illustrations FIG. 5-8.

Figure 5:
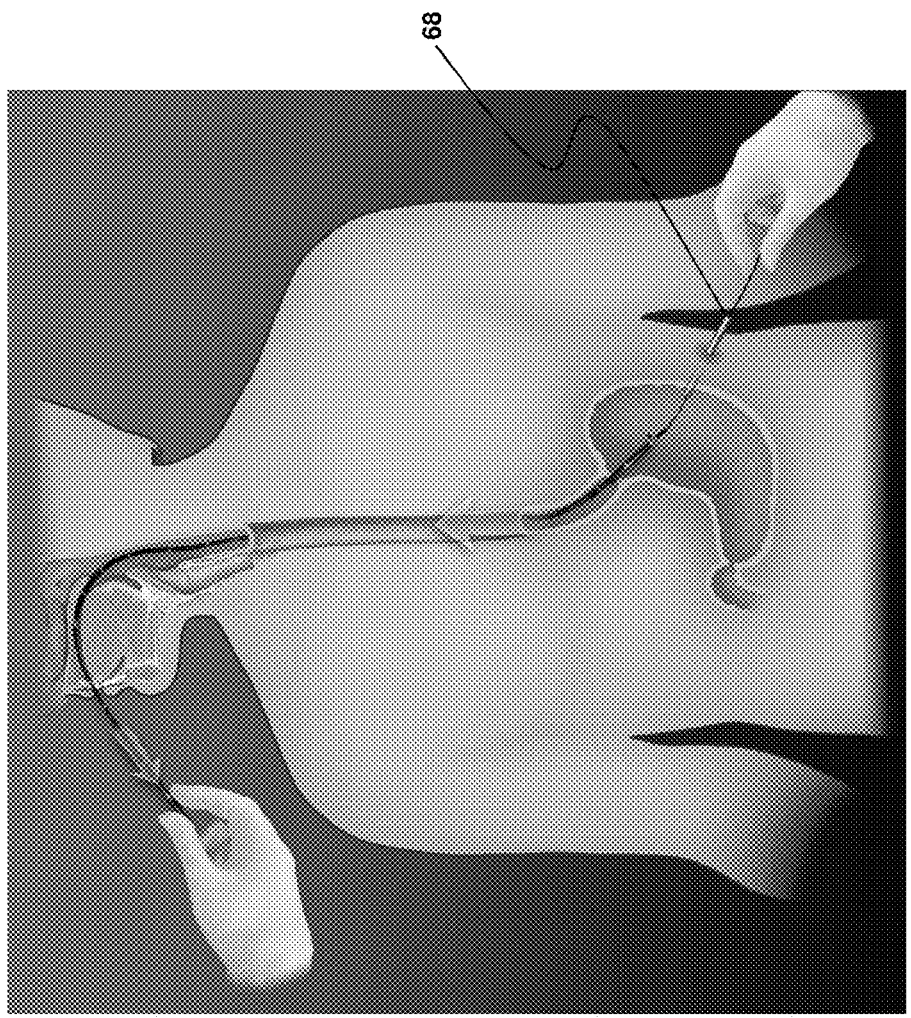
FIG. 5. Guidewire insertion through the abdominal and gastric wall, up the esophagus and out of the patient mouth.
Figure 6:
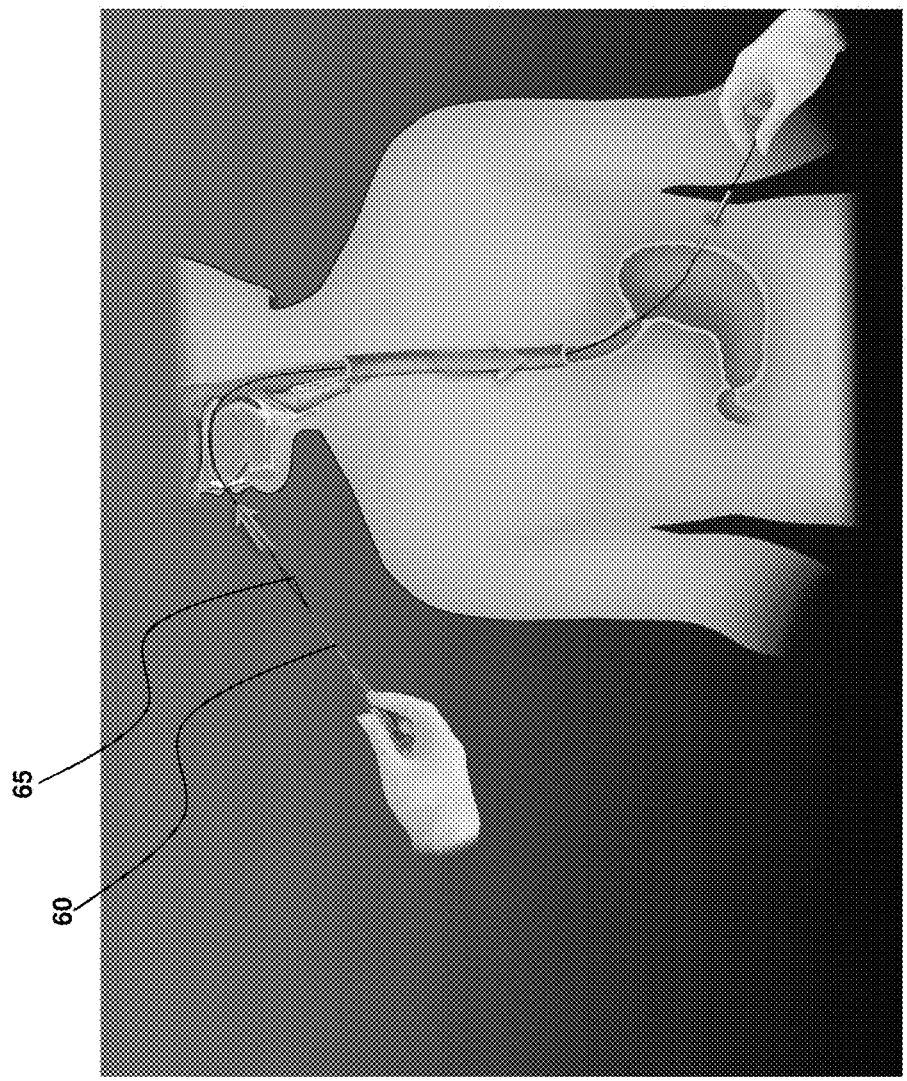
FIG. 6. Guidewire connection to a capture element of an introducer-system that is ready for retrograde introduction.
Figure 7:
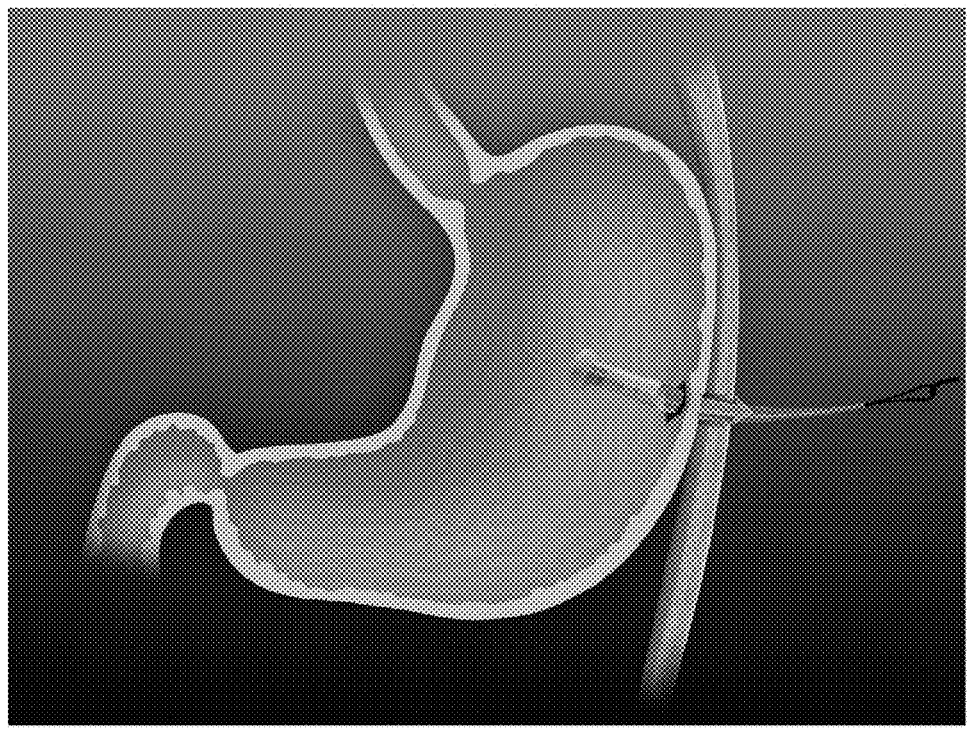
FIG. 7 Retrograde introduction of the introducer-system to the gastric environment, by pulling the guidewire away from the abdominal incision, thereby forcing the introducer through the abdominal wall incision.
Figure 16:
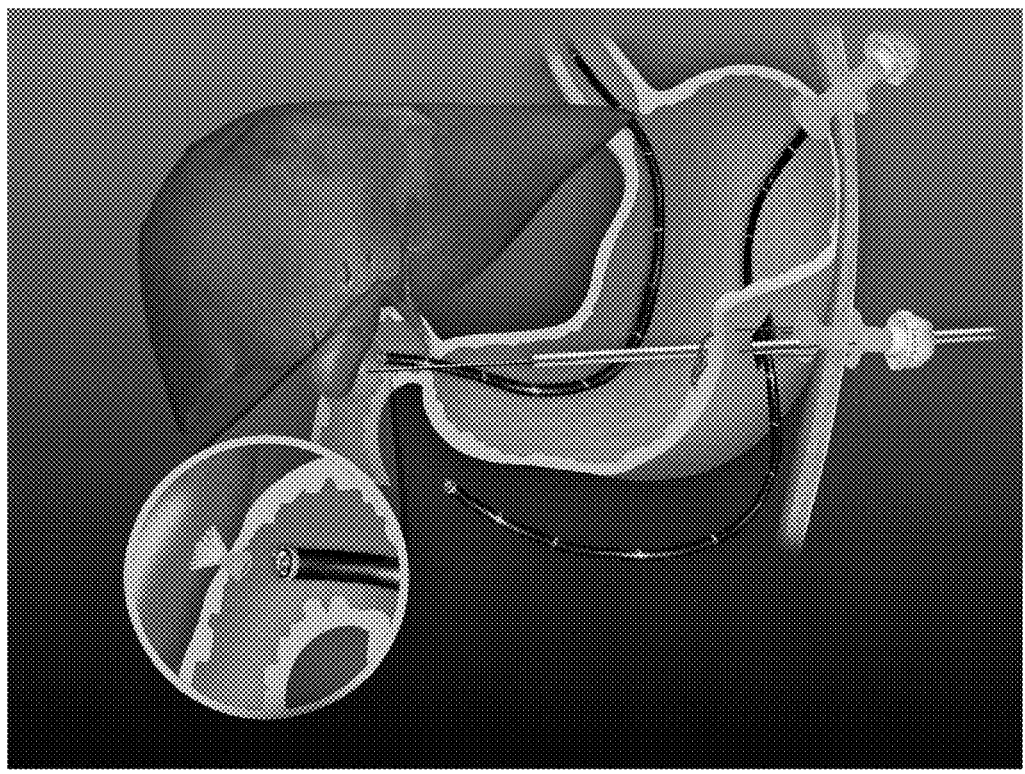
FIG. 16. Use of the system illustrating a cannula anchored to the gastric surface and a second cannula anchored to the peritoneal surface for simultaneous intra- and extra-luminal access, such as for gall bladder drainage.

Briefly, in steps 1000, 1010 and FIG. 5 a guidewire is inserted through an abdominal wall and into the stomach lumen, including using a standard or modified Seldinger technique. This guidewire may be directly inserted from the abdominal wall and into the stomach lumen. In step 1020, a capture element of the introducer is connected to the guidewire at one end. At the other end of the introducer the trans-abdominal gastric system is connected thereto (FIG. 6). The guidewire is then pulled in a retrograde direction, as shown in FIGS. 6-7 and step 1030 to introduce the system through the oral-pharynx, esophagus and into the stomach lumen, so that the internal anchor contacts the stomach wall (FIG. 8). In contrast, for a system that is to be anchored to the peritoneal wall, the system may be positioned with an internal anchor resting against the gastric wall, sutures prepositioned, and the internal anchor pulled entirely through the gastric wall and into position against the peritoneal surface (see, e.g., FIG. 25, illustrating one system 10 anchored to the gastric wall and a second system 10A anchored to the peritoneal surface), with similar steps thereafter. Sutures are pre-positioned through the gastric wall, via the abdominal wall, in step 1031, including by the various steps outlined in FIG. 9 including steps 1161 of FIG. 9. In this manner, irrespective of the final end position of the internal anchor (e.g., internal anchor positioned against the inner-facing peritoneal surface 1035 or internal anchor positioned against the inner-facing stomach wall 1031), upon procedure completion, the defect in the gastric wall and abdominal wall are readily closed via the pre-positioned sutures. In step 1040, the introducer is removed. The external anchor and cap (FIG. 8) are connected to the system, so that the system is reliably anchored to the abdominal wall (step 1050), thereby providing a working channel to the stomach lumen 1060 for subsequent applications, as desired. As will be appreciated, an equivalent methodology is employed to provide system anchoring to the peritoneal surface to provide extra-luminal access relative to the stomach lumen. This is illustrated in step 1035, wherein the internal anchor is pulled through the stomach wall and subsequently secured to the inner-facing peritoneal surface, with equivalent steps 1040 and 1050 used to provide a working channel 1065 to the peritoneal space, and thereby providing extra-luminal access. This is explicitly illustrated with system 10A of FIG. 24, and opening 200 in the gastric wall formed by system 10A. As desired, pre-closure elements may be pre-positioned through the gastric wall and aligned with the abdominal wall in a manner equivalent to that summarized in FIGS. 9-13. This is an efficient and effective closure system that avoids the often time-consuming and laborious end-surgical routine of aligning the gastric wall incision with the abdominal wall incision before. FIG. 16 illustrates two pre-closure sutures passing through the abdominal and gastric walls, with the cannula system anchored to the perineal cavity to provide intra-peritoneal and extra-luminal access. In this manner, the pre-closure sutures ensure the defects in the gastric and abdominal walls are aligned and readily sutured upon surgical completion.

Example 5: Removal Methods

Figure 9:
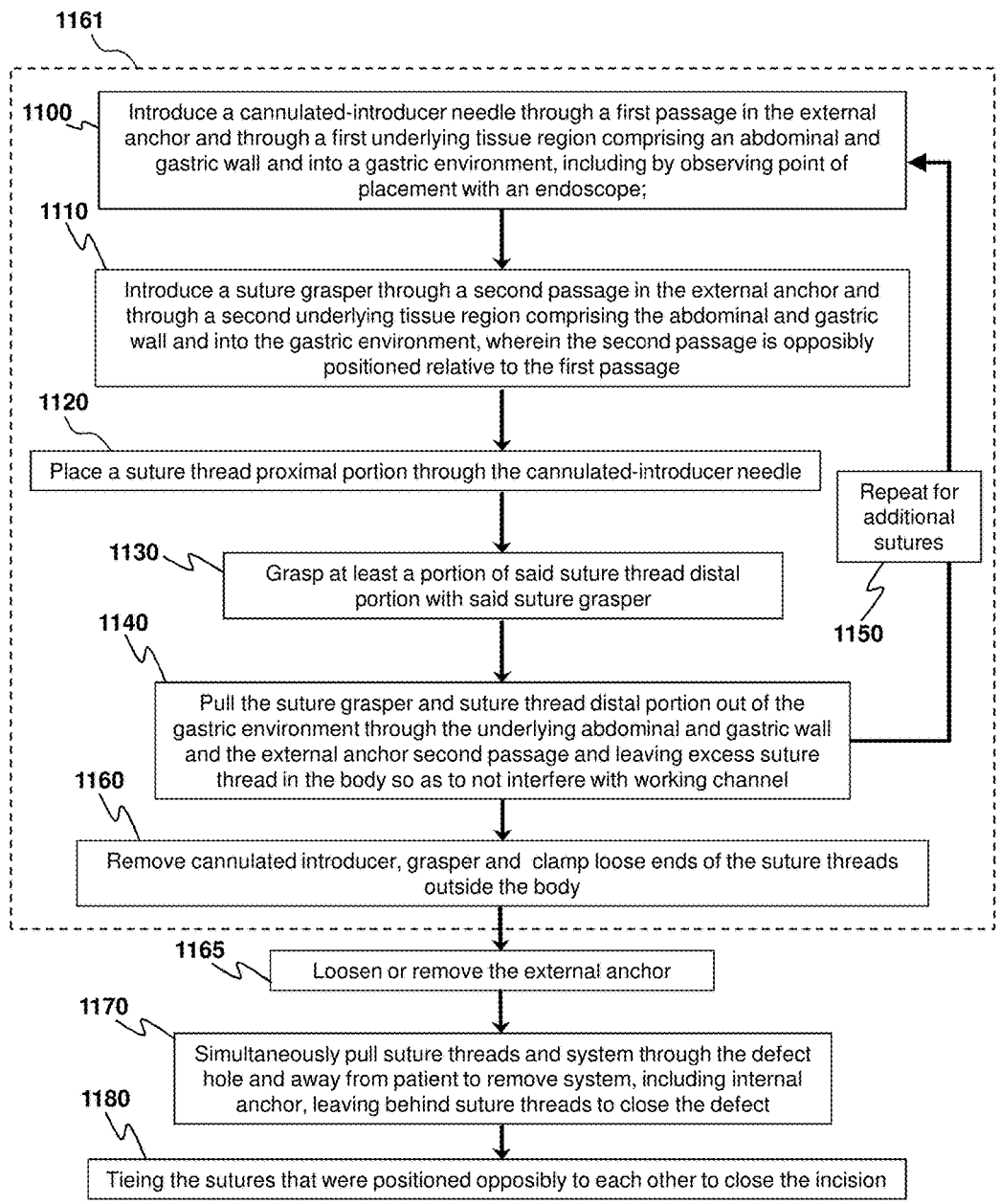
FIG. 9. Flow chart summary of a method of removing the system; and as schematically illustrated in FIGS. 10-13.
Figure 11:
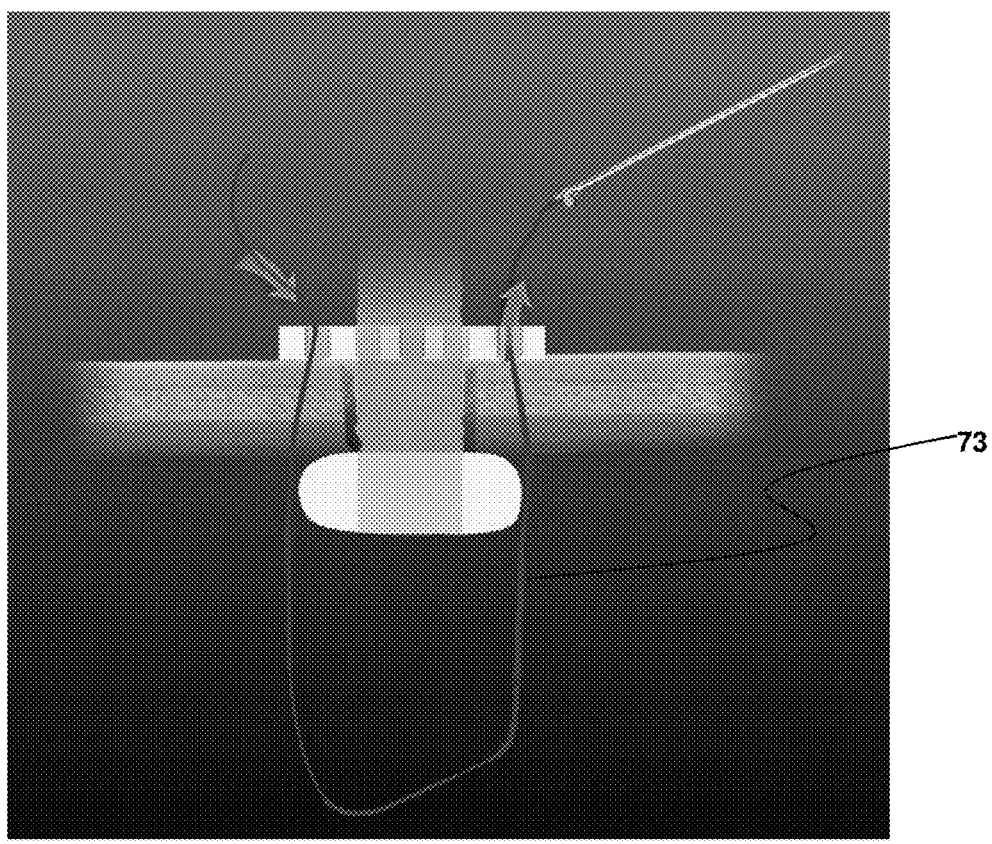
FIG. 11. The suture thread of FIG. 11 is grasped and pulled out of the patient with a grasper that traverses a second external anchor passage that is opposibly positioned relative to the first external anchor passage.
Figure 12:
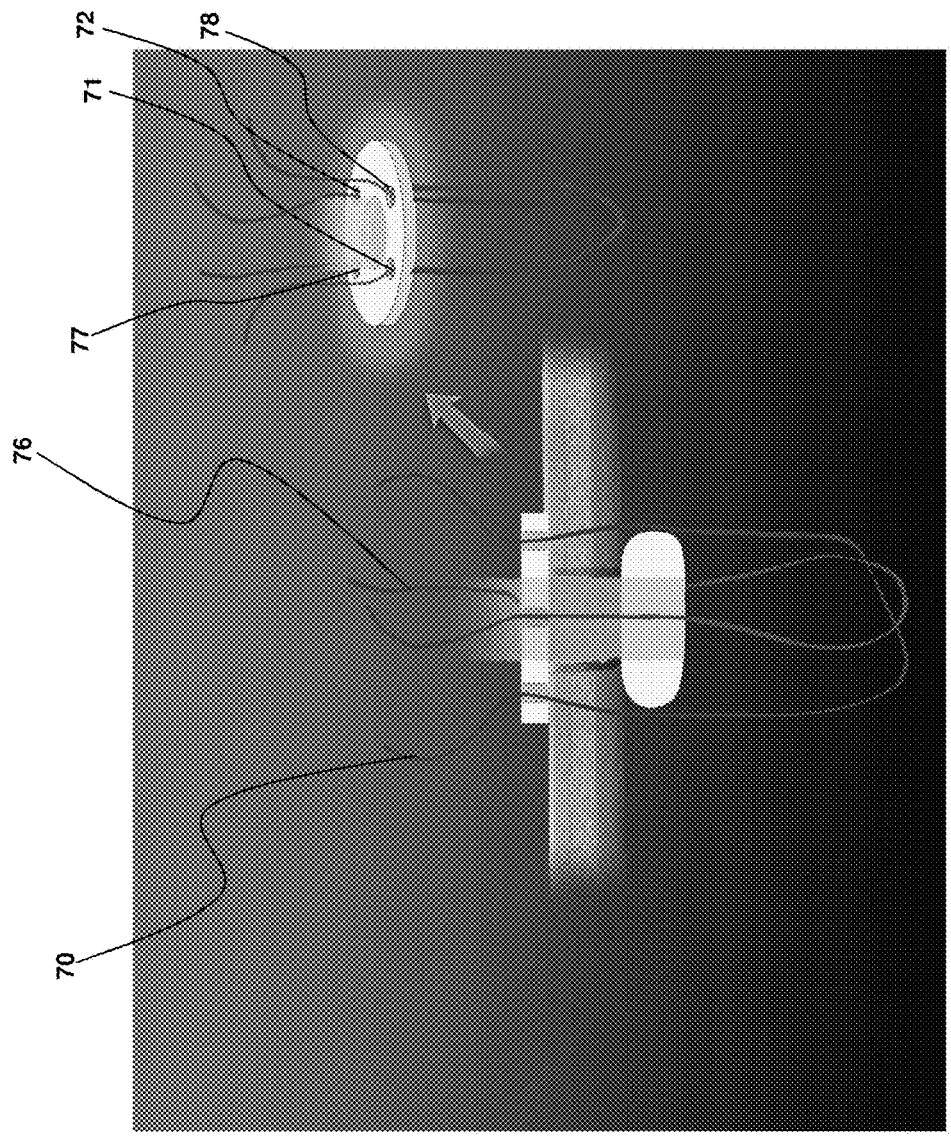
FIG. 12. The steps outlined in FIGS. 10-11 are repeated for a second suture thread.
Figure 13:
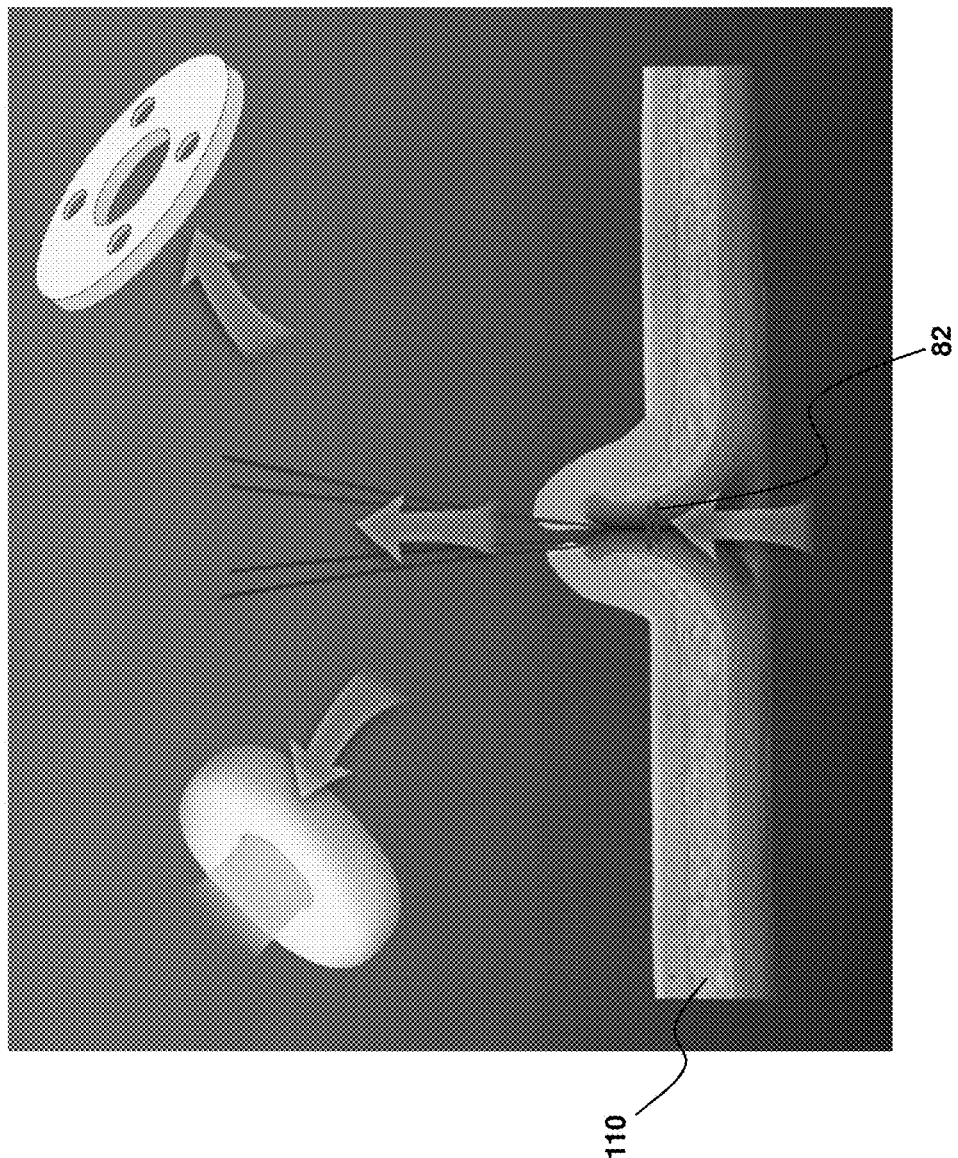
FIG. 13. The system and accessible suture threads are pulled so that all suture threads and the internal anchor are pulled outside the abdominal wall, thereby suturing the incision closed.

An example of a method for removing the system in a safe and effective manner is summarized in the flow chart of FIG. 9 and corresponding illustrations FIG. 10-13. Passages 49 in the external anchor facilitate controlled suture positioning at the start of a surgical procedure. In steps 1100 and 1110, cannulated introducer needle 80 and suture grasper 81 are positioned through first passage 71 and second passage 72, respectively (FIG. 10) and underlying tissue into the gastric space. A suture thread is grasped and pulled through passage 71 and out of passage 72, thereby providing a threaded loop around the outermost portion of the internal anchor (FIG. 11 and steps 1120 1130 and 1140). As desired, steps 1100-1140 are repeated to obtain additional suture threads at different orientations from each other (FIG. 12 and repeating step 1150). The suture thread ends are pulled away from the patient to remove the system and internal and external anchors, thereby providing sutures 82 outside the abdominal wall 110 (FIG. 13 and steps 1160 1165 1170 1180). This method is simple and reliable, while minimizing the risk of infection or other complications associated with conventional trocar insertion methods. Box 1161 includes those steps that may be used to pre-position sutures during the introduction summarized in FIG. 4 at step 1031. The steps outside box 1161 are those that are used to tie the pre-positioned sutures to close the defects in all walls after procedure completion.

Example 6: Applications

Because the systems described herein provide reliable and complication-free access to the abdominal cavity, gastric lumen, or both (see, e.g., FIGS. 14-16, 23-24), the systems are compatible with a wide range of applications, including surgical applications. Any conventional endoscopic or laparoscopic instrument may be used with the instant transabdominal gastric surgical systems, including to achieve triangulation with either two or one systems. Various tissues and regions are similarly accessible, either directly or indirectly, with one or more medical instruments. For example, the system may be positioned through the skin and abdominal wall to provide access to the intraperitoneal or retroperitoneal space. Similarly, the system may be positioned through the skin, abdominal wall, and the stomach wall to provide intra-gastric or stomach lumen access. Similarly, use of two systems may provide simultaneous and independent access to both the intraperitoneal space and intra-gastric space. Such a platform is extremely versatile with respect to accessing various organs or regions of the body in an elegant and minimally disruptive manner. For example, from the gastric lumen, various surgical procedures on the stomach wall are performed. In addition, the esophagus and gastrointestinal tract are readily accessed.

Figure 14:
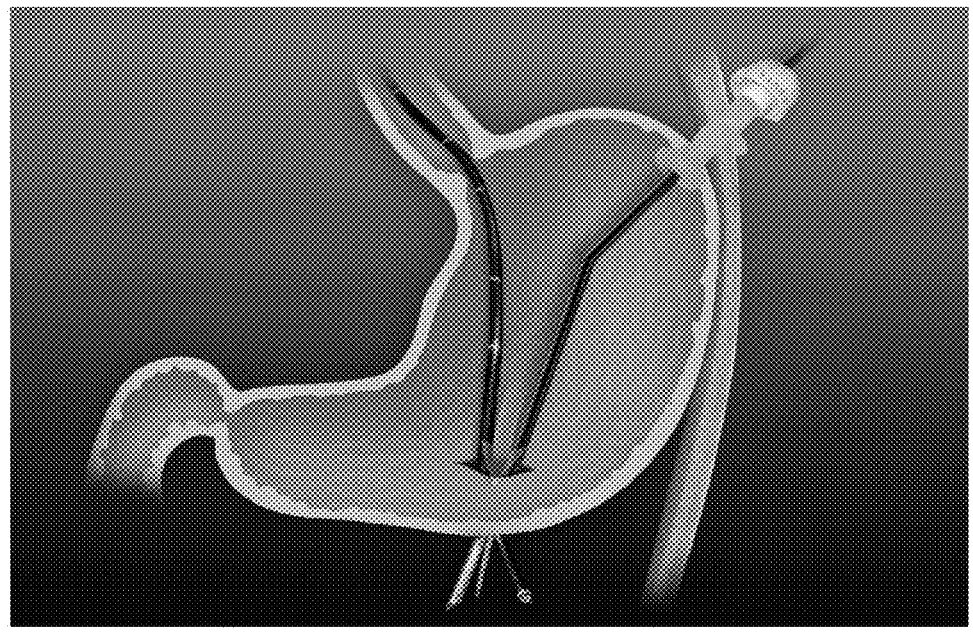
FIG. 14. Stomach incision for accessing intra-peritoneal space made by trans-abdominal gastric system placement with internal bumper pulled thru the gastric wall and positioned against the peritoneal surface (not shown, but see FIG. 16).
Figure 15:
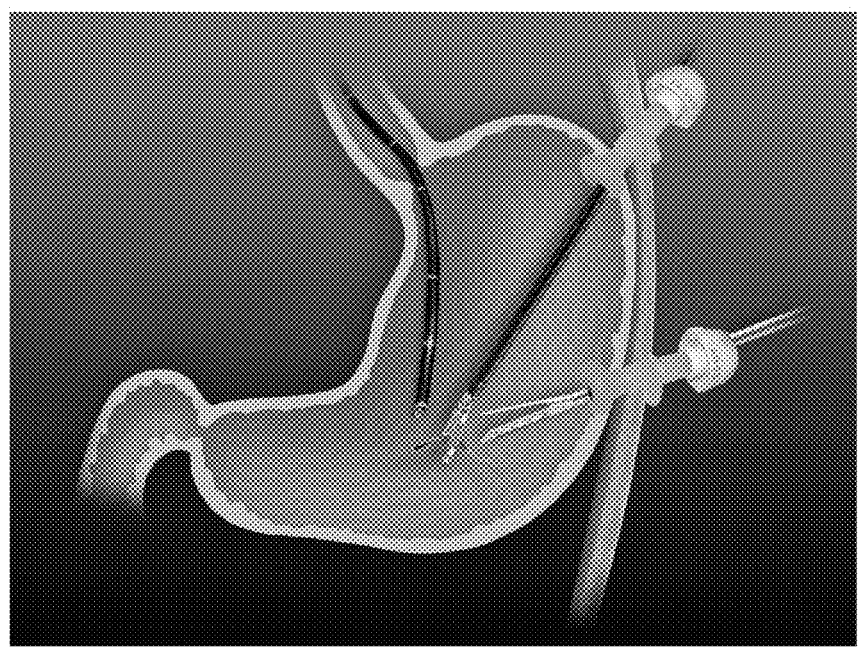
FIG. 15 Triangulation with two trans-abdominal gastric systems and an endoscope.

Furthermore, the intraperitoneal and retroperitoneal space can be accessed from the stomach lumen via an incision through the stomach wall by a trans-abdominal gastric system that has been pulled through the stomach wall (FIG. 14 or 16). Medical instruments in the stomach lumen, from outside the patient, can then pass through the stomach wall incision for an operative procedure in the intraperitoneal space, an organ or tissue surface associated therewith, or an organ moved into the gastric environment from the intraperitoneal or retroperitoneal space. Examples of tissues and organs that are particularly suited for surgical procedures with the systems and methods described herein includes all abdominal-pelvic organs, including the stomach, gall bladder, liver, pancreas, spleen, esophagus, small intestine, large intestine, pelvic organs and the thoracic cavity.

Examples of various applications are illustrated by the system placements summarized in FIGS. 14-16 and 23-24, and include, for example, endoscopic suturing/stapling, GI tract surgeries, surgery in the peritoneal, retroperitoneal and/or intragastric space, tissue manipulation such as grasping, lifting and incision, apposition of tissue edges, refractory GI bleed, resection of gastric gastrointestinal stromal tumors (GIST), hiatal hernia, fundoplication and gall bladder drainage.

Figure 17:
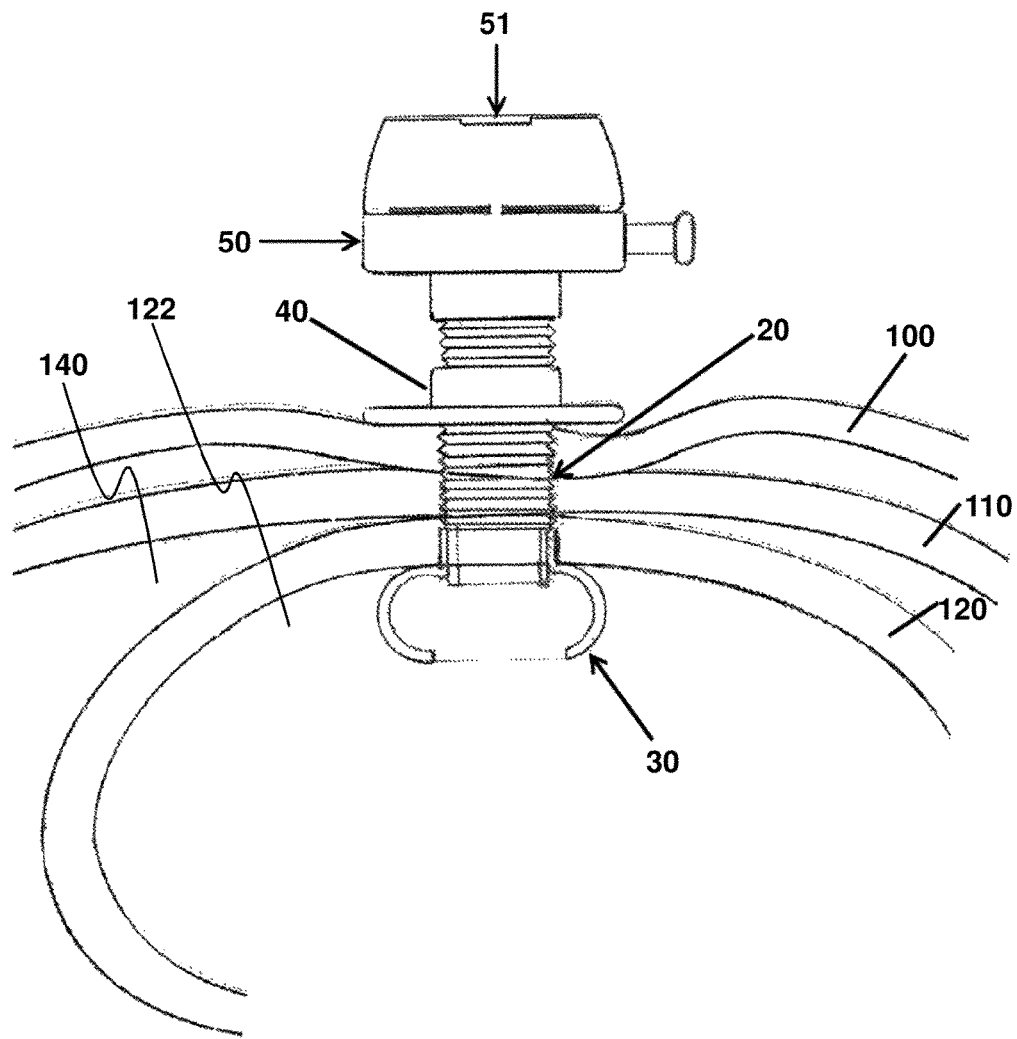
FIG. 17 illustrates a side view of the system in use and spanning from outside the patient through to the gastric environment, with a working channel defined by a cannula of the system disposed therebetween.

FIGS. 17-24 describe, in further detail, other system embodiments and exemplary elements thereof. FIG. 17 is a side view of the system in use and traversing from outside a patient, through the skin 100, abdominal wall 110, and stomach wall 120, so that internal anchor 30 is positioned against an inner surface of the stomach wall 120. External anchor 40 is positioned against the skin 100 in an opposed configuration relative to the internal anchor 30. In this manner, the cannula 20 is reliably secured and ready for long term use. Instrument port 51 in cap 50 is ready to receive a medical device 12 (see, e.g., FIGS. 23-24).

Figure 18:
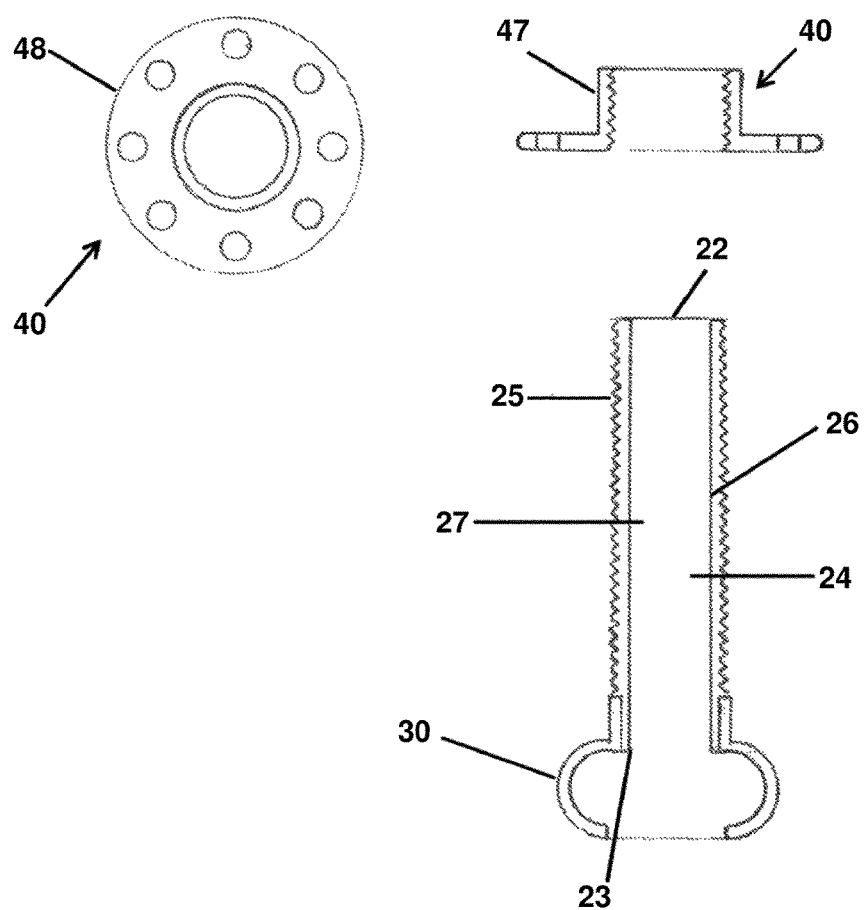
FIG. 18. Top and side view of the external anchor (top left and right panels) and a cross-sectional view of the cannula and internal anchor portion (bottom panel).
Figure 20:
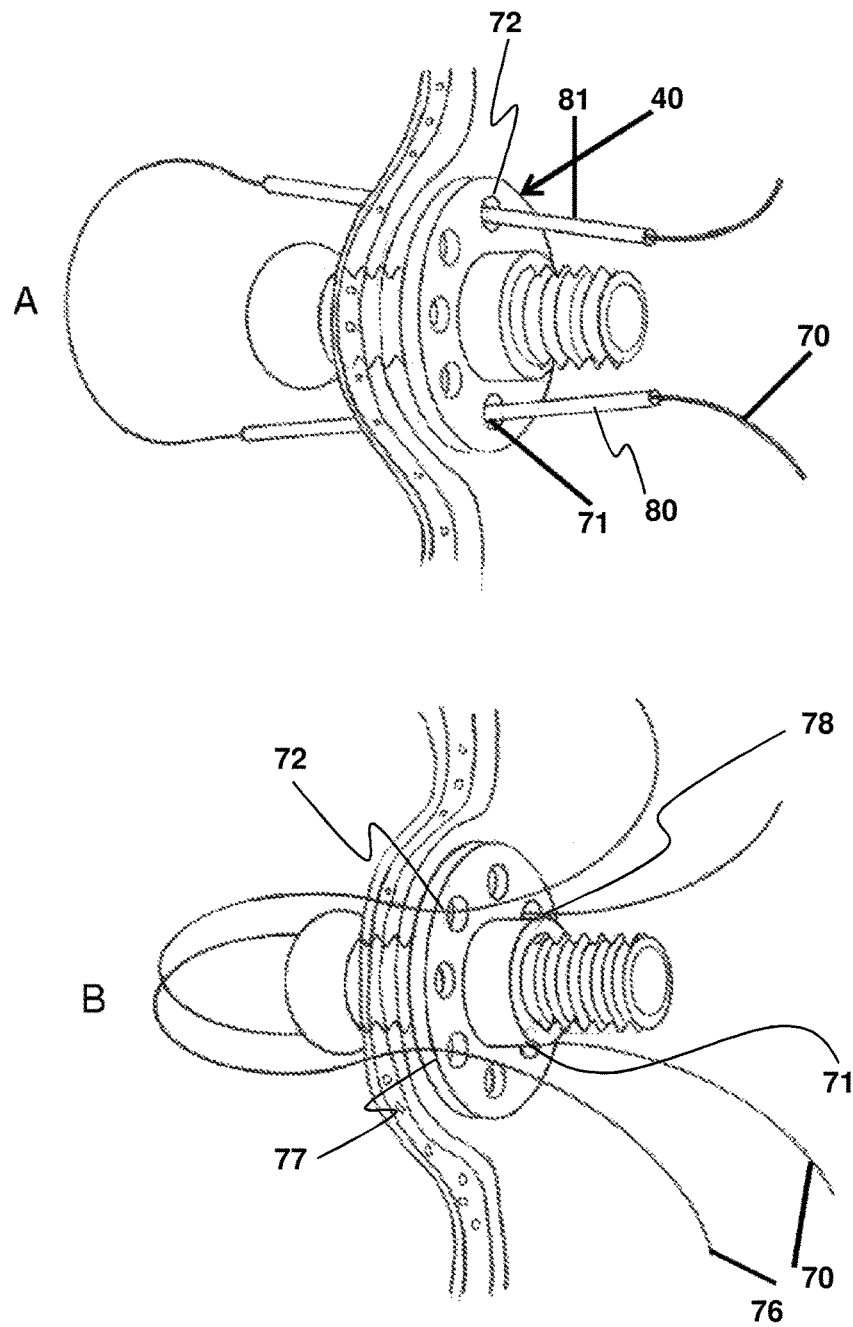
FIG. 20 shows a detailed view of the use of suture threads through the external anchor passages to facilitate system removal. A shows one suture thread. B shows two suture threads.

The external anchor 40 is shown in more detail in FIGS. 18-20. In one embodiment, the external anchor flange is disc-shaped. In another embodiment the external anchor flange 48 outer edge comprises a plurality of straight edges 495, illustrated as an octagon. As shown by the middle right panel of FIG. 19, the passages may be defined by a passage separation distance 490, a minimum separation distance 491 and a maximum separation distance 492 from the central body 47 edge. In contrast to the left panel of FIG. 19B, the passages in the right panel form a circumferential offset pattern.

FIG. 20 shows a detailed view of the use of suture threads 70 76 through the external anchor passages 71 72 and 77 78, respectively, to facilitate system removal.

Figure 21:
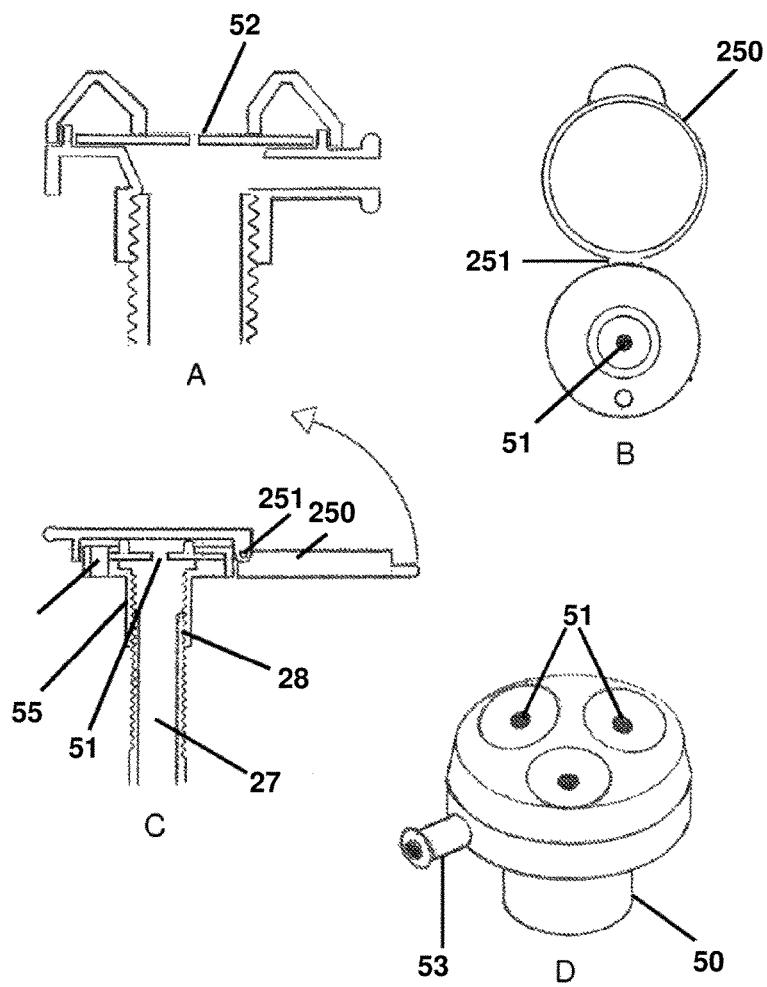
FIG. 21 provides examples of various caps and instrument ports, including A cap side view; B hinged cap top view open configuration; C hinged cap side view; D cap with a plurality of instrument ports and a pressure port.

FIG. 21 provides examples of various caps and instrument ports. A is a cap side view showing the instrument port may be formed from a memory sealant 52 B is a hinged cap with a lid 250 connected via hinge 251 in an open configuration; C Shows a side view of B. A cap 50 having a plurality of instrument ports 51 and a pressure port 53 is shown in D.

Figure 22:
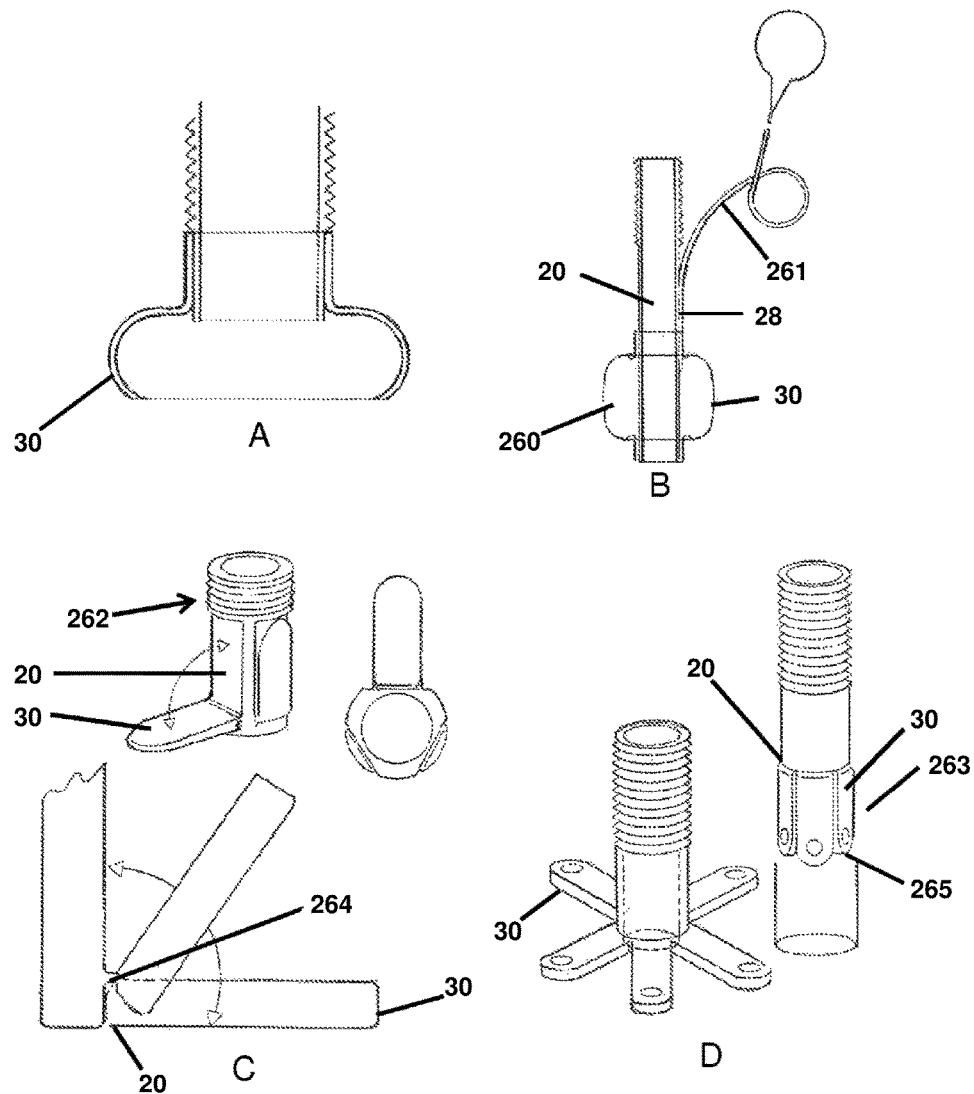
FIG. 22 includes examples of different internal anchor mechanisms, including: A bumper; B balloon; C hinge; and D hinged umbrella.

Examples of different internal anchors are illustrated in FIG. 22, including A bumper. B balloon 260 that provide an adjustable and deployable anchor, via inflation tube 261. C Hinge anchor 262 and D hinged umbrella anchor 263 are examples of deployable internal anchors. Hinge 264 facilitates anchor end 265 movement from a stored to a deployed configuration.

Figure 23:
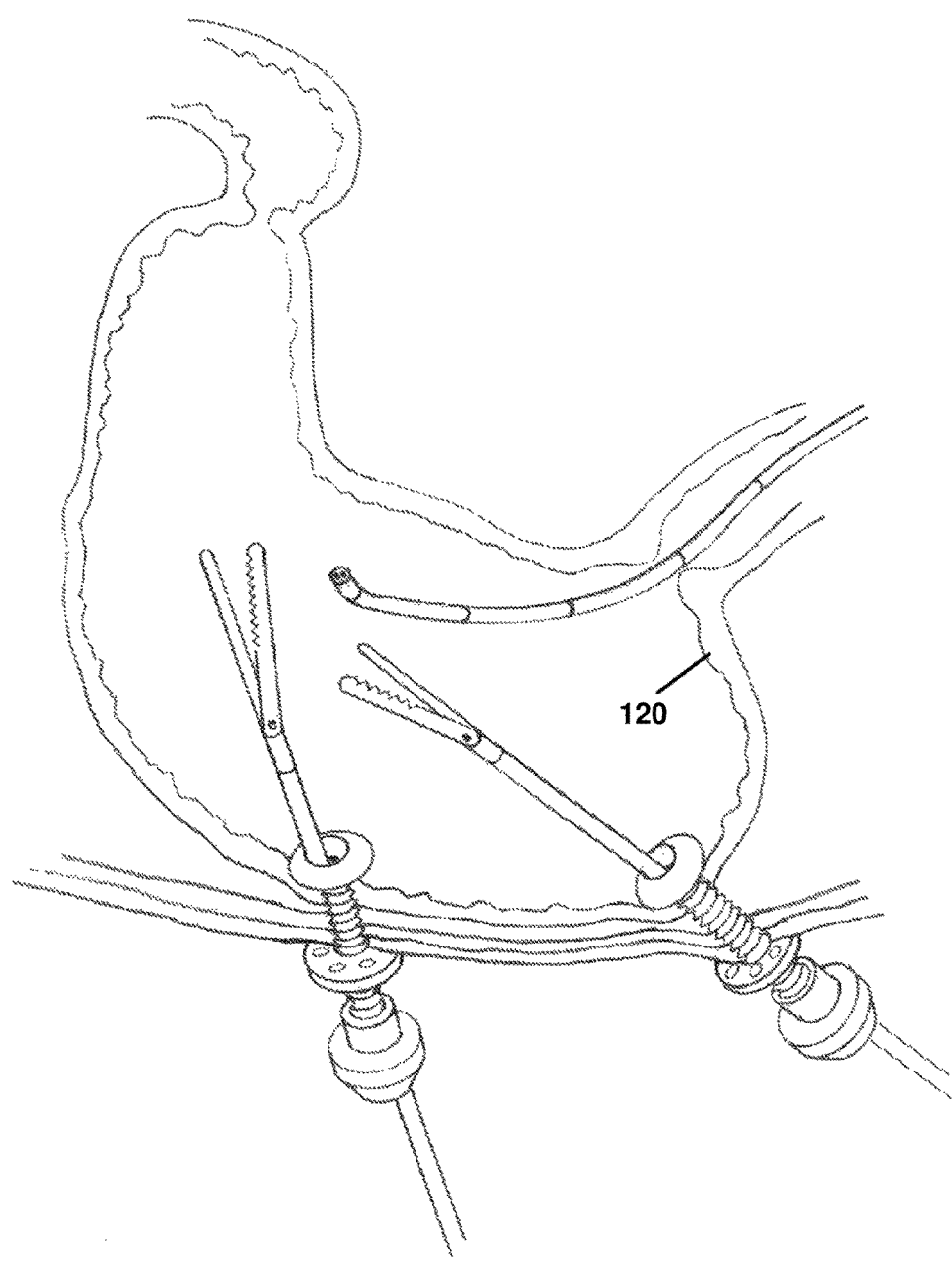
FIG. 23 illustrates an application using two trans-abdominal gastric systems and an endoscope, to provide medical instrument triangulation on a specific lumen gastric region.

FIG. 23 illustrates an application using two systems, to provide medical instrument triangulation on a specific internal or luminal gastric region, including with an endoscope.

Figure 24:
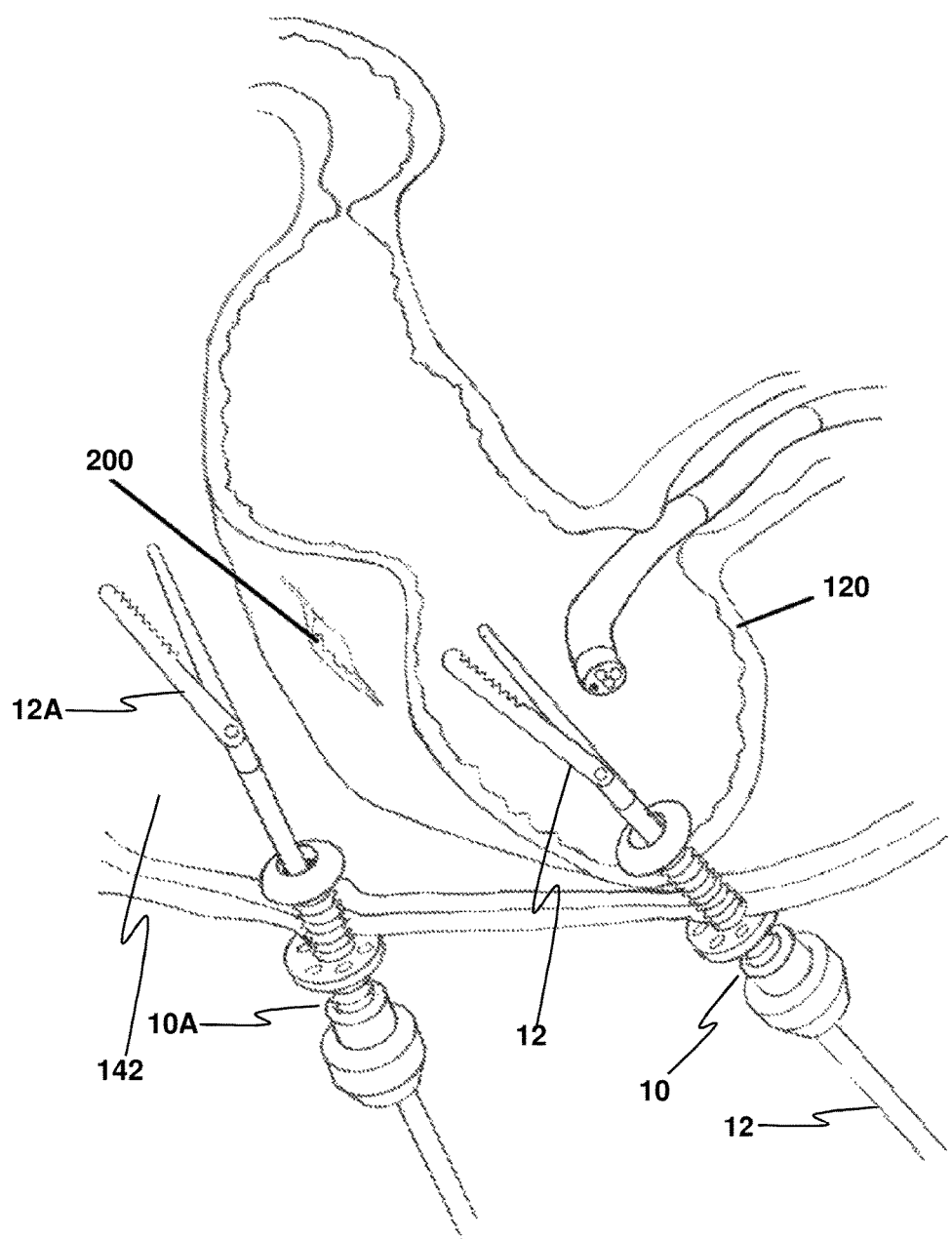
FIG. 24 illustrates access to the peritoneal space with a system that is anchored to the peritoneal surface, such as by a transabdominal gastric system that is pulled through the gastric wall and positioned against the peritoneal surface, with a resultant incision through the gastric wall and available, as desired for access by medical instruments, either intra-luminally or trans-luminally. With this configuration of systems, a tissue may be approached, extralumenally, intralumenally, or both. An endoscope may be used, such as for intra- and/or extra-luminal visualization

FIG. 24 illustrates access to the peritoneal space 142 with a system 10A that is anchored to the peritoneal surface. Also illustrated is an incision 200 in the gastric wall formed by the trans-abdominal gastric system with the internal anchor pulled through the gastric wall and then positioned against the peritoneal surface, so that system 10A may be introduced via retrograde introduction in a manner similar to system 10. With this configuration of systems, tissue may be approached, extralumenally by device 12A via system 10A, intralumenally by device 12 via system 10, or both extralumenally and intralumenally. For simplification, pre-closure suture elements illustrated in FIG. 16 are not shown in FIGS. 23-24.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a size range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that materials, biological materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A trans-abdominal gastric surgical system comprising:
   a cannula having:
     an outer end;
     an inner end;
     a central portion having an outer-facing surface that extends between said inner end and said outer end and an inner-facing surface that defines a lumen configured to receive a portion of a medical instrument that traverses between said outer end and said inner end;
   an internal anchor connected to said inner end and having a surface shape configured to secure the system against an interior surface of a gastric wall or peritoneal surface;
   an external anchor removably and translationally connected to said cannula outer-facing surface and having a surface shape configured to secure said system against a skin surface;
   a cap removably connected to said cannula outer end; and
   a stopcock connected to said cap for providing controlled access to said cannula lumen.

2. The system of claim 1, wherein said internal anchor surface shape is adjustable, deployable, or both.

3. The system of claim 2, wherein said internal anchor is selected from the group consisting of: a balloon; a hinged umbrella; and a flexible bumper.

4. The system of claim 1, wherein said internal anchor encircles said cannula inner end and is configured to secure said system to an interior surface of a gastric wall or an interior surface of a peritoneal cavity.

5. The system of claim 1, wherein said internal anchor comprises a bumper and said bumper and said cannula are formed from a unitary material.

6. The system of claim 5, wherein said bumper has:
   a curved outer surface with a maximum diameter that is greater than or equal to 2 cm and less than or equal to 4 cm;
   a height that is greater than or equal to 0.5 cm and less than or equal to 2.5 cm;
   an open exit having a diameter that is less than or equal to 3.5 cm; and
   a hollow interior volume defined by said curved outer surface and through which a medical device can traverse.

7. The system of claim 1, wherein said external anchor comprises a disc having an inner-facing surface that defines a passage for receiving said cannula.

8. The system of claim 7, wherein said translationally connected disc and cannula outer-facing surface comprises a matched internal thread and external thread pair on facing surfaces of said disc inner-facing surface and said cannula outer-facing surface, wherein rotation of said disc relative to said cannula outer-facing surface translates said disc along at least a portion of said cannula outer-facing surface.

9. The system of claim 7, wherein said disc comprises:
   a central body that defines said passage; and
   a flange connected to said central body, said flange comprising a plurality of passages extending therethrough.

10. The system of claim 9, wherein the plurality of passages are arranged in a circumferential offset pattern relative to a central body having a substantially circular shape.

11. The system of claim 10, wherein adjacent passages are separated by a separation distance that is greater than 1 mm and less than 4 mm and have alternating separation distances from said central body corresponding to a minimum separation distance and a maximum separation distance.

12. The system of claim 11, wherein said flange has an outer edge that is an octagon shape and the plurality of passages number eight, the plurality of passages comprising four corner-positioned passages and four side-positioned passages with adjacent corners separated by an individual side-positioned passage, with the corner-positioned passages separated from the central body by the maximum separation distance and the side-positioned passage separated from the central body by the minimum separation distance, wherein each of the plurality of passages is positioned adjacent to a corner region of the octagon shape flange outer edge.

13. The system of claim 9, further comprising a plurality of suture threads, wherein each individual suture thread traverses a pair of opposed passages.

14. The system of claim 1, said cap comprising one or more instrument ports configured for introducing one or more medical instruments to said cannula lumen and out of said inner end and into a patient when the system is anchored to a gastric wall or a peritoneal surface by said internal anchor and a skin surface by said external anchor.

15. The system of claim 14, said cap comprising a plurality of instrument ports formed from a memory sealant, each instrument port having an independently selected size and introduction angle.

16. The system of claim 1, further comprising a pressure port operably connected to said cap for measuring or controlling pressure at said cannula inner end.

17. The system of claim 1, having an external anchor removed configuration for said external anchor removed from said cannula, the system further comprising an introducer removably connected to said cannula outer end in said external anchor removed configuration.

18. The system of claim 17, wherein said introducer comprises a receiving opening that removably receives said cannula outer end and at least a portion of said cannula central portion.

19. A trans-abdominal gastric surgical system comprising:
a cannula having:
an outer end;
an inner end;
a central portion having an outer-facing surface that extends between said inner end and said outer end and an inner-facing surface that defines a lumen configured to receive a portion of a medical instrument that traverses between said outer end and said inner end;
an internal anchor connected to said inner end and having a surface shape configured to secure the system against an interior surface of a gastric wall or peritoneal surface;
an external anchor removably and translationally connected to said cannula outer-facing surface and having a surface shape configured to secure said system against a skin surface;
an external anchor removed configuration for said external anchor removed from said cannula, the system further comprising an introducer removably connected to said cannula outer end in said external anchor removed configuration;
wherein said introducer comprises:
a receiving opening that removably receives said cannula outer end and at least a portion of said cannula central portion;
a distal end;
a proximal end through which said receiving opening traverses;
a tapered central portion extending between said distal end and said proximal end;
a capture element connected to said distal end; and
wherein said tapered central portion is configured for introducing said system to a patient by retrograde introduction past a patient's oropharynx by pulling a guidewire connected to said capture element in a direction away from a patient surface.

20. The system of claim 19, wherein said introducer has a flexibility or bending moment selected so that said introducer is capable of deforming to follow contours of a patient oral-pharynx and esophagus during insertion in a patient.

21. The system of claim 19, having an introducer removed configuration, wherein in said introducer removed configuration, said external anchor is connected to said cannula outer surface in an external anchor deployed configuration.

22. The system of claim 19, said tapered central portion having:
an angle of incidence at said distal end that is greater than or equal to 5° and less than or equal to 20°;
a total length that is greater than or equal to 2 cm and less than or equal to 15 cm;
a tapered portion extending from said distal end and a substantially untapered portion extending between said proximal end and said tapered portion, having a tapered portion longitudinal length to untapered portion longitudinal length ratio ($L_T/L_U$) that is greater than or equal to 1 and less than or equal to 5; and
wherein said introducer has a flexibility selected so that said introducer is capable of deforming to follow contours of a patient oral-pharynx and esophagus during insertion into a patient.

23. A method of inserting a trans-abdominal gastric surgical system in a patient, the method comprising the steps of:
inserting a guidewire through an abdominal wall insertion and into a stomach lumen;
guiding a portion of said inserted guidewire out of the stomach lumen, through an esophagus and mouth to provide an accessible portion of said guidewire;
connecting a capture element of said introducer of said trans-abdominal gastric surgical system assembly of claim 19 in said external anchor removed configuration to said accessible portion of said guidewire;
pulling the guidewire connected to the capture element of the introducer trans-abdominal gastric surgical assembly in a direction away from the patient so the assembly is introduced into the stomach lumen;
continuing to pull the guidewire out through said abdominal wall incision to advance the introducer portion of said assembly out of the stomach through said abdominal wall incision so that an internal anchor of said trans-abdominal gastric surgical system contacts an inner-facing surface of the stomach;
removing said introducer from said assembly to reveal an exposed end of said trans-abdominal gastric surgical system;
connecting said external anchor to said exposed end of said trans-abdominal gastric surgical system; and
moving said external anchor in a direction toward a skin surface of the patient to contact the skin surface in a position that faces said internal anchor to reliably secure said trans-abdominal gastric surgical system to the patient;
thereby inserting said trans-abdominal gastric surgical system.

24. The method of claim 23, further comprising the step of attaching a cap to said exposed end of said inserted trans-abdominal gastric surgical system.

25. The method of claim 24, further comprising the step of introducing one or more than one surgical instruments through the trans-abdominal gastric surgical system for use in a procedure selected from the group consisting of: instrument triangulation; accessing a stomach lumen; accessing a retroperitoneal space; manipulating tissue; closing an incision; a gastric surgery; a gall bladder surgery; single or simultaneous access to an upper GI tract and small intestinal lumen; access of an intra-peritoneal space; and access of an extra-peritoneal space and associated organs.

26. The method of claim 23, further comprising the step of:
placing a plurality of pre-sutures through the gastric and abdominal wall.

27. The method of claim 26, further comprising the step of temporally resting said internal anchor against a luminally-facing gastric surface;

pulling said internal anchor through the gastric wall, thereby providing an open insertion through the gastric wall with said plurality of pre-sutures around said gastric wall insertion; and securing said internal anchor to an inner-facing surface of an abdominal wall.

28. The method of claim 24, further comprising the step of removing the trans-abdominal gastric surgical system after procedure completion by:

inserting at a start of or before the procedure a plurality of sutures by:

introducing a cannulated-introducer needle through a first passage in the external anchor and through a first underlying tissue region comprising an abdominal and gastric wall and into a gastric environment;

introducing a suture grasper through a second passage in the external anchor and through a second underlying tissue region comprising the abdominal and gastric wall and into the gastric environment, wherein the second passage is opposibly positioned relative to the first passage;

placing a suture thread proximal portion through the cannulated-introducer needle;

guiding a suture thread distal portion past an outer-facing surface of the internal anchor, wherein the suture thread distal portion longitudinally extends from the suture thread proximal portion;

grasping at least a portion of said suture thread distal portion with said suture grasper;

pulling the suture grasper and suture thread distal portion out of the gastric environment and through the underlying abdominal and gastric wall and the external anchor second passage, wherein the suture thread portion in the body is positioned around or beyond said internal anchor to avoid interference with an instrument introduced through a working channel formed by the trans-abdominal gastric surgical system;

repeating the above steps with a second suture thread positioned through a third external anchor passage, fourth external anchor passage, and corresponding third and fourth underlying tissue regions comprising the abdominal and gastric wall;

removing the cannulated-introducer needle and the suture grasper to reveal matched pairs of suture thread proximal and distal portions;

loosening or removing the external anchor from said exposed end of said trans-abdominal gastric surgical system;

removing the trans-abdominal gastric surgical system in a direction that pulls the internal anchor through the stomach and abdominal wall and pulling the revealed matched pairs of suture thread proximal and distal portions in a direction away from the patient, thereby removing the trans-abdominal gastric surgical system from the patient; and suturing the suture threads in a position that is outside the abdominal wall thereby closing an abdominal and stomach wall defect formed by the step of removing the trans-abdominal gastric surgical system.

* * * * *